United States Patent [19]
Lee et al.

[11] Patent Number: 5,847,162
[45] Date of Patent: Dec. 8, 1998

[54] 4,7-DICHLORORHODAMINE DYES

[75] Inventors: Linda Lee, Palo Alto; Scott C. Benson, Oakland; Barnett B. Rosenblum, San Jose; Sandra L. Spurgeon, San Mateo, all of Calif.

[73] Assignee: The Perkin Elmer Corporation, Foster City, Calif.

[21] Appl. No.: 672,196

[22] Filed: Jun. 27, 1996

[51] Int. Cl.$^6$ .......................... C07D 311/88; C12Q 1/68; C07H 19/00
[52] U.S. Cl. .......................... 549/227; 549/356; 549/381; 549/385; 435/6; 536/22.1
[58] Field of Search .......................... 435/6; 536/22.1; 549/356, 381, 385, 227

[56] References Cited

U.S. PATENT DOCUMENTS

| | | | |
|---|---|---|---|
| 4,318,846 | 3/1982 | Khanna et al. | 260/112 B |
| 4,855,225 | 8/1989 | Fung et al. | 435/6 |
| 5,188,934 | 2/1993 | Menchen et al. | 435/6 |
| 5,366,860 | 11/1994 | Bergot et al. | 435/6 |

FOREIGN PATENT DOCUMENTS

| | | | |
|---|---|---|---|
| 0 252 683 | 7/1987 | European Pat. Off. | C07H 21/04 |
| 45263 | 11/1887 | Germany . | |
| 47451 | 11/1887 | Germany . | |
| 108347 | 11/1898 | Germany . | |
| 2049503 | 4/1971 | Germany | C07D 7/42 |
| 2049527 | 4/1971 | Germany | C07D 7/42 |
| 3425631 | 1/1986 | Germany | C09B 11/28 |
| 12433/70 | 2/1973 | Switzerland | D06P 3/76 |
| WO 91/03476 | 3/1991 | WIPO | C07D 21/04 |
| WO 91/05060 | 4/1991 | WIPO . | |
| WO 91/07507 | 5/1991 | WIPO | C12Q 1/68 |
| WO 94/05688 | 3/1994 | WIPO | C07H 21/00 |

Primary Examiner—Ardin H. Marschel
Assistant Examiner—Jezia Riley
Attorney, Agent, or Firm—Paul D. Grossman

[57] ABSTRACT

A class of 4,7-dichlororhodamine compounds useful as fluorescent dyes are disclosed having the structure

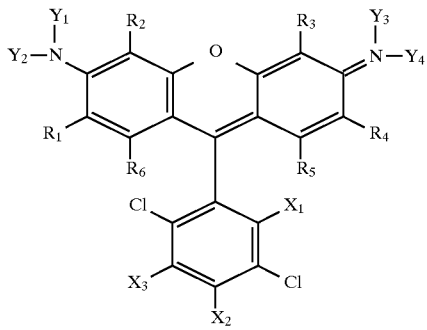

wherein $R_1$–$R_6$ are hydrogen, fluorine, chlorine, lower alkyl lower alkene, lower alkyne, sulfonate, sulfone, amino, amido, nitrile, lower alkoxy, lining group, or combinations thereof or, when taken together, $R_1$ and $R_6$ is benzo, or, when taken together, $R_4$ and $R_5$ is benzo; $Y_1$–$Y_4$ are hydrogen or lower alkyl or, when taken together, $Y_1$ and $R_2$ is propano and $Y_2$ and $R_1$ is propano, or, when taken together, $Y_3$ and $R_3$ is propano and $Y_4$ and $R_4$ is propano; and $X_1$–$X_3$ taken separately are selected from the group consisting of hydrogen, chlorine, fluorine, lower alkyl carboxylate, sulfonic acid, —CH$_2$OH, and linking group. In another aspect, the invention includes reagents labeled with the 4,7-dichlororhodamine dye compounds, including deoxynucleotides, dideoxynucleotides, and polynucleotides. In an additional aspect, the invention includes methods utilizing such dye compounds and reagents including dideoxy polynucleotide sequencing and fragment analysis methods.

15 Claims, 15 Drawing Sheets

AAAGTGTAAAGCCTGGGGTGCCTAATGAGTGAGCTAACTCACA

ATTCGTA ATCATGGTC AT AGCT GT T TCCT GTGT G AAAT T GT T AT

FIG. 8E    FIG. 8F    FIG. 8G

4, 7-DICHLORORHODAMINE DYES

FIELD OF THE INVENTION

This invention relates generally to fluorescent dye compounds useful as molecular probes. More specifically, this invention relates to 4,7-dichlororhodamine dyes useful as fluorescent labeling reagents.

REFERENCES

*ABI PRISM™ 377 DNA Sequencer User's Manual*, Rev. A, Chapter 2, The Perkin-Elmer Corporation, Foster City, Calif. (p/n 903433) (1995).
Bergot, J. B., et al., U.S. Pat. No. 5,366,860 (1994)
Bergstrom, et al., *JACS*, 111: 374–375 (1989)
Caskey et al., U.S. Pat. No. 5,364,759 (1994)
Connell et al., *Biotechniques*, 5: 342–348 (1987)
Eckstein ed., *Oligonucleotides and Analogs*, Chapters 8 and 9, IRL Press (1991)
Eckstein, *Oligonucleotides and Analogues*, IRL Press (1991)
Fung et al., U.S. Pat. No. 4,757,141 (1988)
Fung et al., U.S. Pat. No. 4,855,225 (1989)
Gait, *Oligonucleotide Synthesis*, IRL Press (1990)
Gebeyehu et al, *Nucleic Acids Research*, 15: 4513–4535 (1987)
Gibson et al., *Nucleic Acids Research*, 15: 6455–6467 (1987)
Haralambidis et al, *Nucleic Acids Research*, 15: 4856–4876 (1987)
Haugland, *Molecular Probes Handbook of Fluorescent Probes and Research Chemicals*, Molecular Probes, Inc. (1992)
Hermanson, *Bioconjugate Techniques*, Academic Press (1996)
Hobbs et al., *J Org. Chem.*, 54: 3420 (1989)
Hobbs et al., U.S. Pat. No. 5,151,507 (1992)
Hunkapiller, et al., U.S. Pat. No. 4,811,218(1989)
Innis et al. eds., *PCR Protocols*, Academic Press (1990)
Ju et al., *Proc. Natl. Acad Sci. USA* 92: 4347–4351 (1995)
Kasai, et al., *Anal. Chem.*, 47: 34037 (1975)
Khanna, et al., U.S. Pat. No. 4,318,846 (1988)
Lee et al. *Nucleic Acids Research*, 21: 3761–3766 (1993)
Madabhushi, et al., International Patent Application No. WO US94/13852 (1994)
Maniatis et al., *Biochemistry*, 14: 3787–3794 (1975)
Maniatis, *Methods in Enzymology*, 65: 299–305 (1980)
Menchen, et al., U.S. Pat. No. 5,188,934 (1993)
Mullis, U.S. Pat. No. 4,683,202 (1987)
Nelson et al., *Nucleosides and Nucleotides*, 5(3): 233–241 (1986)
Nelson, *Nucleic Acids Research* 20(23): 6253–6259 (1992a)
Nelson, U.S. Pat. No. 5,141,813 (1992b)
Nelson, U.S. Pat. No. 5,401,837 (1995)
Orgel et al., *Nucleic Acids Research* 11(18): 6513 (1983)
Osterman, *Methods of Protein and Nucleic Acid Research*, Vol. 1 Springer-Verlag (1984)
Pringle et al., *DNA Core Facilities Newsletter*, 1: 15–21 (1988)
Prober et al., *Science*, 238: 336–341 (1987)
Rickwood and Hames, eds., *Gel Electrophoresis of Nucleic Acids: A Practical Approach*, IRL Press (1981)
Sanger, et al., *Proc. Natl. Acad Sci. USA* 74: 5463–5467 (1977)
Scheit, *Nucleotide Analogs*, John Wiley (1980)
Smith et al., *Nucleic Acids Research*, 113: 2399–2412 (1985)
Smith et al., U.S. Pat. No. 5,118,800 (1992)
Steiner ed., *Excited States of Biopolymers*, Plenum Press (1983)
Stryer, *Biochemistry*, W. H. Freeman (1981)
Vos et al., *Nucleic Acids Research*, 23(21): 4407–4414 (1995)
Ward, et al., U.S. Pat. No. 5,559,767 (1995)
Webber, U.S. Pat. No. 5,075,217 (1991)
Wheeless et al, *Flow Cytometry: Instrumentation and Data Analysis*, pgs. 21–76, Academic Press (1985)
Woo, et al., U.S. Pat. No. 5,231,191 (1993)

BACKGROUND

The non-radioactive detection of biological analytes is an important technology in modem analytical biotechnology. By eliminating the need for radioactive labels, safety is enhanced and the environmental impact of reagent disposal is greatly reduced, resulting in decreased costs for analysis. Examples of methods utilizing such non-radioactive detection methods include DNA sequencing, oligonucleotide probe methods, detection of polymerase-chain-reaction products, immunoassays, and the like.

In many applications the independent detection of multiple spatially overlapping analytes in a mixture is required, e.g., single-tube multiplex DNA probe assays, immuno assays, multicolor DNA sequencing methods, and the like. In the case of multi-loci DNA probe assays, by providing multicolor detection, the number of reaction tubes may be reduced thereby simplifing the experimental protocols and facilitating the manufacturing of application-specific kits. In the case of automated DNA sequencing, multicolor labeling allows for the analysis of all four bases in a single lane thereby increasing throughput over single-color methods and eliminating uncertainties associated with inter-lane electrophoretic mobility variations.

Multiplex detection imposes a number of severe constraints on the selection of dye labels, particularly for analyses requiring an electrophoretic separation and treatment with enzymes, e.g., DNA sequencing. First, it is difficult to find a collection of dyes whose emission spectra are spectrally resolved, since the typical emission band half-width for organic fluorescent dyes is about 40–80 nanometers (nm) and the width of the available spectrum is limited by the excitation light source. Second, even if dyes with non-overlapping emission spectra are found, the set may still not be suitable if the respective fluorescent efficiencies are too low. For example, in the case of DNA sequencing, increased sample loading cannot compensate for low fluorescence efficiencies (Pringle). Third, when several fluorescent dyes are used concurrently, simultaneous excitation becomes difficult because the absorption bands of the dyes are widely separated. Fourth, the charge, molecular size, and conformation of the dyes must not adversely affect the electrophoretic mobilities of the fragments. Finally, the fluorescent dyes must be compatible with the chemistry used to create or manipulate the fragments, e.g., DNA synthesis solvents and reagents, buffers, polymerase enzymes, ligase enzymes, and the like.

Because of these severe constraints only a few sets of fluorescent dyes have been found that can be used in multicolor applications, particularly in the area of four-color DNA sequencing (Smith 1992, 1995; Prober; Connell).

One class of fluorescent dyes particularly useful in multicolor applications are the rhodamine dyes, e.g., tetramethylrhodamine (TAMRA), rhodamine X (ROX), rhodamine 6G (R6G), rhodamine 110 (R110), and the like (13ergot).

Rhodamine dyes are particularly attractive relative to fluorescein dyes because (1) rhodainines are typically more photostable than fluoresceins, (2) rhodamine-labeled dideoxynucleotides are better substrates for thermostable polymerase enzymes, and (3) the emission spectra of rhodamine dyes is significantly to the red (higher wavelength) of fluoresceins.

However, one important drawback of presently available rhodamine dyes in the context of multiplex detection methods is the relatively broad emission spectrum of such dyes. This broad emission spectrum results in poor spectral resolution between spectrally neighboring dyes thereby making the multicomponent analysis of such dye combinations difficult. The fluorescence emission spectra shown in FIG. 7A demonstrate this high degree of spectral overlap. A second drawback of currently available rhodamine dyes is that their absorption spectrum does not match the wavelength of currently available solid state frequency-doubled green diode lasers, e.g., neodymium solid-state YAG lasers, which have an emission line at approximately 532 nm. It is highly advantageous to use such lasers because of their compact size, long useful life, and efficient use of power.

SUMMARY

The present invention is directed towards our discovery of a class of 4,7-dichlororhodamine dyes useful as molecular probes.

It is an object of the invention to provide a class of rhodamine dyes which have emission spectra which are substantially narrower than presently available rhodamine dyes.

It is another object of the invention to provide a class of rhodamine dyes which have an absorption spectrum shifted by approximately 15 nm to the red as compared to existing rhodamine dyes.

In a first aspect, the foregoing and other objects of the invention are achieved by an a compound having the formula:

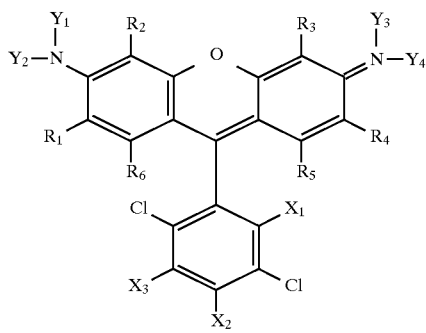

wherein the variable substituents are defined as follows. $R_1$–$R_6$ taken separately are hydrogen, fluorine, chlorine, lower alkyl, lower alkene, lower alkyne, sulfonate, sulfone, amino, amido, nitrile, lower alkoxy, linking group, or combinations thereof, or, when taken together, $R_1$ and $R_6$ is benzo, or, when taken together, $R_4$ and $R_5$ is benzo. Preferably, $R_1$–$R_6$ are hydrogen, methyl or ethyl. $Y_1$–$Y_4$ taken separately are hydrogen or lower alkyl or, when taken together, $Y_1$ and $R_2$ is propano and $Y_2$ and $R_1$ is propano, or, when taken together, $Y_3$ and $R_3$ is propano and $Y_4$ and $R_4$ is propano. $X_1$–$X_3$ taken separately are hydrogen, chlorine, fluorine, lower alkyl, carboxylate, sulfonic acid, —CH$_2$OH, and linking group. Preferably, $X_1$ is carboxylate and $X_2$ and $X_3$ taken separately are hydrogen or linking group.

In a second aspect, the invention includes a labeled nucleotide having the formula:

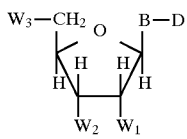

wherein the variable substituents and linkages are defined as follows. D is the 4,7-dichlororhodamine dye compound of the invention. B is a 7-deazapurine, purine, or pyrimidine nucleotide base, preferably uracil, cytosine, deazaadenine, or deazaguanosine. $W_1$ and $W_2$ taken separately are H or OH. $W_3$ is OH, —PO$_4$, —P$_2$O$_7$, —P$_3$O$_{10}$, including analogs thereof In one preferred embodiment, $W_1$ is H, $W_2$ is OH, and $W_3$ is —P$_3$O$_{10}$. In a second preferred embodiment, $W_1$ and $W_2$ are H and $W_3$ is —P$_3$O$_{10}$. When B is purine or 7-deazapurine, the sugar moiety is attached at the $N^9$-position of the purine or deazapurine, and when B is pyrimidine, the sugar moiety is attached at the $N^1$-position of the pyrimidine. The linkage linking B and D is attached to D at one of positions $R_1$–$R_6$ or $X_1$–$X_3$. Preferably, the linkage linking B and D is attached to D at one of positions $X_2$ or $X_3$. In a particularly preferred embodiment, the linkage is

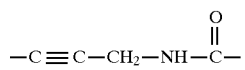

If B is a purine, the linkage is attached to the 8-position of the purine, if B is 7-deazapurine, the linkage is attached to the 7-position of the 7-deazapurine, and if B is pyrimidine, the linkage is attached to the 5-position of the pyrimidine.

In a third aspect, the invention includes a labeled polynucleotide containing a nucleotide having the formula:

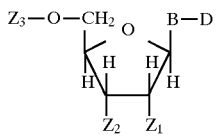

wherein the variable substituents and linkages are defined as follows. D is a 4,7-dichlororhodamine dye compound of the invention. B is a 7-deazapurine, purine, or pyrimidine nucleotide base, preferably uracil, cytosine, deazaadenine, or deazaguanosine. $Z_1$ is H or OH. $Z_2$ is H, OH, —PO$_4$, or Nuc, a neighboring nucleotide, wherein Nuc and the nucleoside are linked by a phosphodiester linkage or analog thereof, the linkage being attached to the 5'-position of Nuc. $Z_3$ is H, —PO$_3$, including phosphate analogs, or Nuc, wherein Nuc and the nucleoside are linked by a phosphodiester linkage or analog thereof, the linkage being attached to the 3'-position of Nuc. When B is purine or 7-deazapurine, the sugar moiety is attached at the $N^9$-position of the purine or deazapurine, and when B is pyrimidine, the sugar moiety is attached at the $N^1$-position of the pyrimidine. The linkage linking B and D is attached to D at one of positions $R_1$–$R_6$ or $X_1$–$X_3$. Preferably, the linkage linking B and D is attached to D at one of positions $X_2$ or $X_3$. In a particularly preferred embodiment, the linkage is

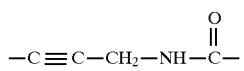

If B is a purine, the linkage is attached to the 8-position of the purine, if B is 7-deazapurine, the linkage is attached to the 7-position of the 7-deazapurine, and if B is pyrimidine, the linkage is attached to the 5-position of the pyrimidine.

In a fourth aspect, the present invention includes a method of polynucleotide sequencing, such method including the following steps. Forming a mixture of a first, a second, a third, and a forth class of polynucleotides such that each polynucleotide in the first class includes a 3'-terminal dideoxyadenosine and is labeled with a first dye, each polynucleotide in the second class includes a 3'-terminal dideoxycytidine and is labeled with a second dye, each polynucleotide in the third class includes a 3'-terminal dideoxyguanosine and is labeled with a third dye, and, each polynucleotide in the forth class includes a 3'-terminal dideoxythymidine and is labeled with a forth dye. The dyes are selected such that one of the first, second, third, or forth dyes is a 4,7-dichlororhodamine dye of the invention, the other of the dyes being spectrally resolvable from the 4,7-dichlororhodamine dye and from each other. Electrophoretically separating the polynucleotides thereby forming bands of similarly sized polynucleotides, illuminating the bands with an illumination beam capable of causing the dyes to fluoresce, and, identifying the classes of the polynucleotides in the bands by the fluorescence spectrum of the dyes.

These and other aspects, objects, features, and advantages of the present invention will become better understood with reference to the following description, drawings, and appended claims.

BRIEF DESCRIPTION OF THE DRAWINGS

FIGS. 8A–8H show preferred syntheses for the preparation of the dye compounds of the present invention.

DETAILED DESCRIPTION OF THE PREFERRED EMBODIMENTS

Figure 1A:
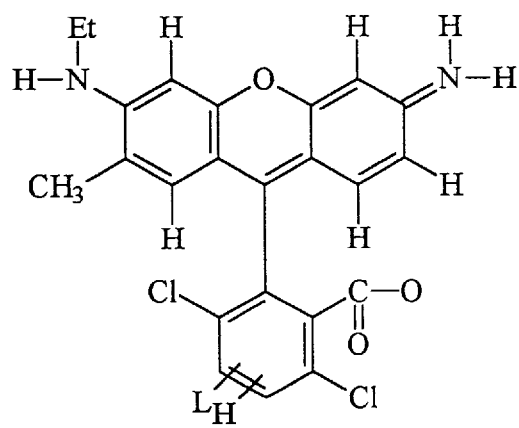
FIGS. 1A–1F show the structures of several preferred embodiments of the dye compounds of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises a novel class of 4,7-dichlororhodamine compounds useful as fluorescent dyes, reagents employing such dyes as molecular labels, and methods utilizing such dyes and reagents in the area of analytical biotechnology. The compounds of the present invention find particular application in the area of multicolor fluorescent DNA sequencing and fragment analysis.

The invention is based in part on the discovery that the fluorescent properties of 4,7-dichlororhodamines and related dyes are highly favorable for use as molecular probes. Their emission band widths are generally 20–30 percent narrower than analogs lacking the 4,7-dichloro derivatives, and, their emission and absorption maxima are at wavelengths generally about 10–30 nm higher than analogs lacking the 4,7-dichloro derivatives.

I. DEFINITIONS

Unless stated otherwise, the following terms and phrases as used herein are intended to have the following meanings:

"Linking group" (L) refers to a functionality capable of reacting with a "complementary functionality" attached to a reagent, such reaction forming a "linkage" connecting a dye to a reagent. The particular linking group used depends on the nature of the complementary functionality and the type of linkage desired. In some cases, the linking group must be activated prior to reaction with a complementary functionality, e.g., the activation of a carboxylate linking group with dicyclohexylcarbodiimide and N-hydroxysuccinimide to form a N-hydroxysuccinimide (NHS) ester. Preferably, whenever the complementary functionality is amine, the linking group of the invention is isothiocyanate, isocyanate, acyl azide, NHS ester, sulfonyl chloride, aldehyde or glyoxal, epoxide, carbonate, aryl halide, imidoester, carbodiimide, anhydride, 4,6-dichlorotriazinylamine, or other active carboxylate. Preferably, whenever the complementary functionality is sulfhydryl, the lining group is haloacetyl alkyl halide, maleimide, halo acetyl, aziridine, acryloyl, arylating agent, e.g., fluorobenzene, and the like. When the complementary functionality is carboxylate, the linking group is preferably diazoalane, diazoacetyl, carbonyldiimidazole, and carbodilmide (Hermanson). In a particularly preferred embodiment, the linking group is an activated NHS ester which reacts with an amine complementary functionality, where to form the activated NHS ester, a dye of the invention including a carboxylate linking group is reacted with dicyclohexylcarbodiimide and N-hydroxysuccinimide to form the NHS ester (Khanna; Kasai). Table 1 below shows a sampling of representative linking groups along with compatible complementary functionalities and resulting linkages.

TABLE 1

| Linking Group | Complementary Functionality | Linkage |
|---|---|---|
| —NCS | —NH₂ | —NHCSNH— |
| ![dichlorotriazine structure: —NH linked to triazine with two Cl] | —NH₂ | ![triazine linkage with —NH— and —NH—] |
| —SO₂X | —NH₂ | —SO₂NH— |
| —C(=O)—O—N(succinimidyl) | —NH₂ | —C(=O)—NH— |
| —NH—C(=O)—CH₂I | —SH | —NH—C(=O)—CH₂S— |
| —N-maleimide | —SH | —N-succinimide-S— |

The term "lower alkyl" denotes straight-chain and branched hydrocarbon moieties containing from 1 to 8 carbon atoms, i.e., methyl, ethyl, propyl, isopropyl, tert-butyl, isobutyl, sec-butyl, neopentyl, tert-pentyl, and the like. The term "propano" in particular refers to the moiety —CH₂CH₂CH₂—. "Lower substituted alkyl" denotes a lower alkyl including electron-withdrawing substituents, such as halo, cyano, nitro, sulfo, and the like. "Lower haloalkyl" denotes a lower substituted alkyl with one or more halogen atom substituents, usually fluoro, chloro, bromo, or iodo. "Lower alkene" denotes a lower alkyl or lower substituted alkyl wherein one or more of the carbon-carbon bonds is a double bond. "Lower alkyne" denotes a lower alkyl or lower substituted allyl wherein one or more of the carbon-carbon bonds is a triple bond. "Sulfonate" denotes moieties comprising a sulfur atom double bonded to two oxygen atoms and single bonded to one oxygen atom, including mono- and di-salts thereof e.g., sodium sulfonate, potassium sulfonate, disodium sulfonate, and the like. "Sulfone" denotes moieties comprising a sulfur atom double bonded to two oxygen atoms. "Amino" refers to moieties including a nitrogen atom bonded to two hydrogen atoms, lower alkyl moieties, or any combination thereof. "Amido" refers to moieties including a carbon atom double bonded to an oxygen atom and single bonded to an amino moiety. "Nitrile" refers to moieties including a carbon atom triple bonded to a nitrogen atom. "Lower Alkoxy" refers to a moiety including lower alkyl single bonded to an oxygen atom. "Aryl" refers to single or multiple phenyl or substituted phenyl, e.g., benzene, naphthalene, anthracene, biphenyl, and the like.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms (Stryer). The term "nucleotide" as used herein refers to a phosphate ester of a nucleoside, e.g., triphosphate esters, wherein the most common site of esterification is the hydroxyl group attached at the C-5 position of the pentose. Many times in the present disclosure the term nucleoside will be intended to include both nucleosides and nucleotides. "Analogs" in reference to nucleosides include synthetic analogs having modified base moieties, modified sugar moieties, and/or modified phosphate ester moieties, e.g., as described elsewhere (Scheit; Eckstein). The term "labeled nucleoside" refers to nucleosides which are covalently attached to the dye compounds of Formula I.

As used herein, the terms "polynucleotide" or "oligonucleotide" refer to linear polymers of natural nucleotide monomers or analogs thereof including double and single stranded deoxyribonucleotides, ribonucleotides, α-anomeric forms thereof and the like. Usually the nucleoside monomers are linked by phosphodiester linkages, where as used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., H, NH₄, Na, and the like if such counterions are present. Polynucleotides typically range in size form a few monomeric units, e.g. 8–40, to several thousands of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

As used herein the term "spectral resolution" in reference to a set of dyes means that the fluorescent emission spectra of the dyes are sufficiently distinct, i.e., sufficiently non-overlapping, that reagents to which the respective dyes are attached, e.g., polynucleotides, can be distinguished on the basis of the fluorescent signal generated by the respective dyes using standard photodetection systems, e.g., employing a system of band pass filters and photomultiplier tubes, a charged-coupled device in conjunction with a spectrograph, or the like, as exemplified by systems described elsewhere (Hunkapiller; Wheeless).

II. 4,7-DICHLORORHODAMINE DYE COMPOUNDS

In a first aspect, the present invention comprises a novel class of 4,7-diclororhodamine dye compounds having the general structure shown immediately below as Formula I. (Note that all molecular structures provided throughout this disclosure are intended to encompass not only the exact electronic structure presented, but also include all resonant structures and protonation states thereof.)

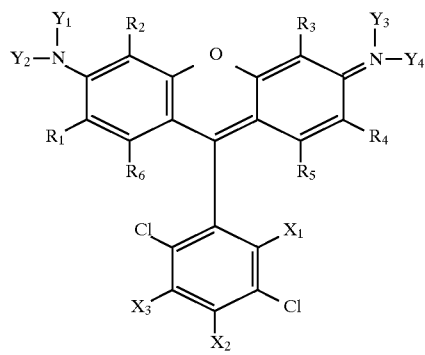

FORMULA I

In Formula I, $R_1$ through $R_6$ taken separately are hydrogen, fluorine, chlorine, lower alkyl, lower alkene, lower alkyne, sulfonate, sulfone, amino, amido, nitrile, lower alkoxy, linking group, or combinations thereof Alternatively, when taken together $R_1$ and $R_6$ is benzo, and/or, $R_4$ and $R_5$ is benzo. In a preferred embodiment, $R_1$ through $R_6$ taken separately are hydrogen, methyl, or ethyl. More preferably, $R_1$ through $R_6$ taken separately are hydrogen or methyl.

$Y_1$ through $Y_4$ taken separately are selected from the group consisting of hydrogen and lower alkyl. Alternatively, $Y_1$ taken together with $R_2$ is propano, and $Y_2$ taken together with $R_1$ is propano, and/or, $Y_3$ taken together with $R_3$ is propano and $Y_4$ taken together with $R_4$ is propano. Preferably, $Y_1$ through $Y_4$ taken separately are hydrogen, methyl, or ethyl.

$X_1$–$X_3$ taken separately are hydrogen, chlorine, fluorine, lower alkyl carboxylate, sulfonic acid, —$CH_2OH$, or linking group. Preferably, $X_1$ is carboxylate. In a preferred embodiment, one of $X_2$ or $X_3$ is linking group.

In one particularly preferred compound of the present invention, referred to herein as DR110, $R_1$–$R_6$ taken separately are hydrogen, $Y_1$–$Y_4$ taken separately are hydrogen, $X_1$ is carboxylate, and one of $X_2$ and $X_3$ is lining group (L), the other being hydrogen. The structure of DR110 is shown below as Formula II.

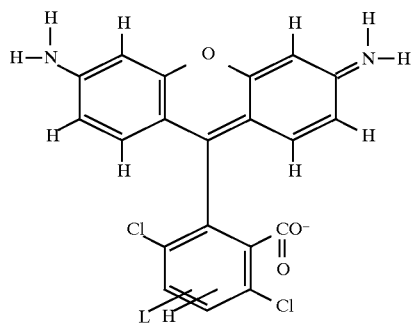

FORMULA II

In a second particularly preferred compound of the present invention, referred to herein as DR6G, $R_1$ and $R_4$ taken separately are methyl, $R_2$, $R_3$, $R_5$, and $R_6$ are hydrogen, one of $Y_1$ and $Y_2$ is ethyl, the other being hydrogen, one of $Y_3$ and $Y_4$ is ethyl, the other being hydrogen, $X_1$ is carboxylate, and one of $X_2$ and $X_3$ is linking group, the other being hydrogen. The structure of DR6G is shown below as Formula III.

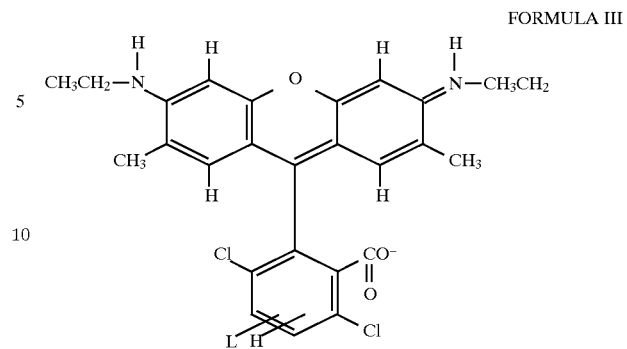

FORMULA III

In a third particularly preferred compound of the present invention, referred to herein as DTMR, $R_1$–$R_6$ taken separately are hydrogen, $Y_1$–$Y_4$ taken separately are methyl, $X_1$ is carboxylate, and one of $X_2$ and $X_3$ is linking group, the other being hydrogen. The structure of DTMR is shown below as Formula IV.

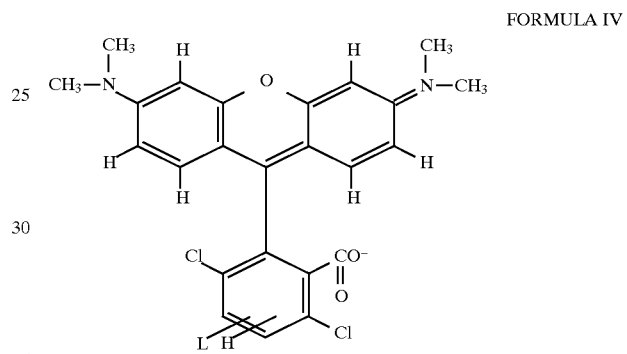

FORMULA IV

In a fourth particularly preferred compound of the present invention, referred to herein as DROX, $R_1$ and $Y_2$ taken together are propano , $R_2$ and $Y_1$ taken together are propano, $R_3$ and $Y_3$ taken together are propano, $R_4$ and $Y_4$ taken together are propano, $R_5$ and $R_6$ are hydrogen, $X_1$ is carboxylate, and one of $X_2$ and $X_3$ is lining group, the other being hydrogen The structure of DROX is shown below as Formula V.

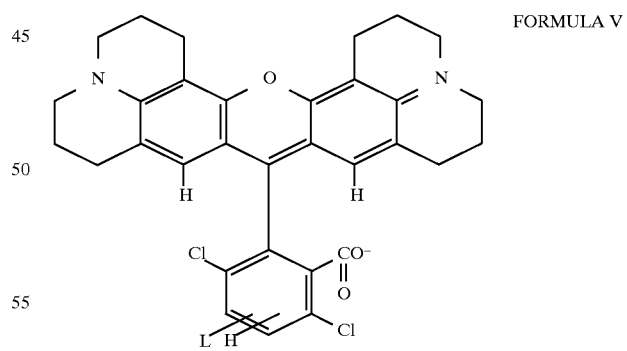

FORMULA V

Figure 1B:
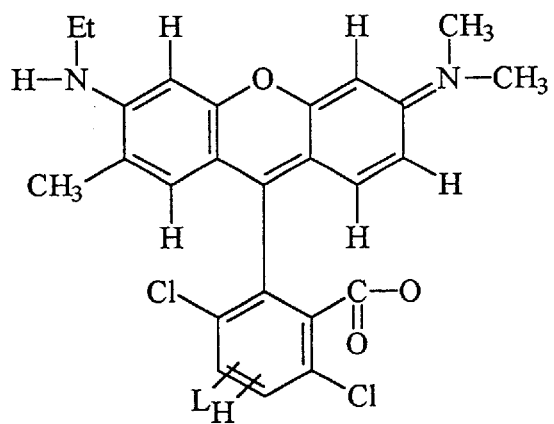
Figure 1C:
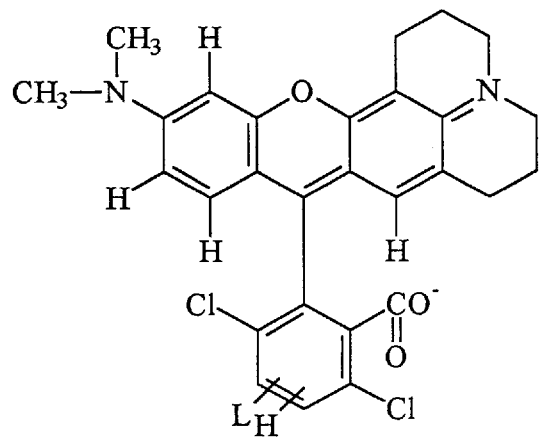
Figure 1D:
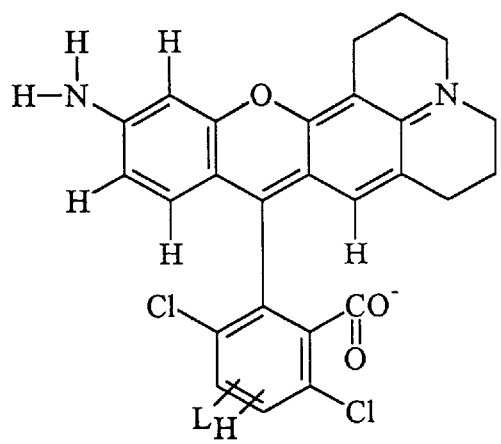
Figure 1E:
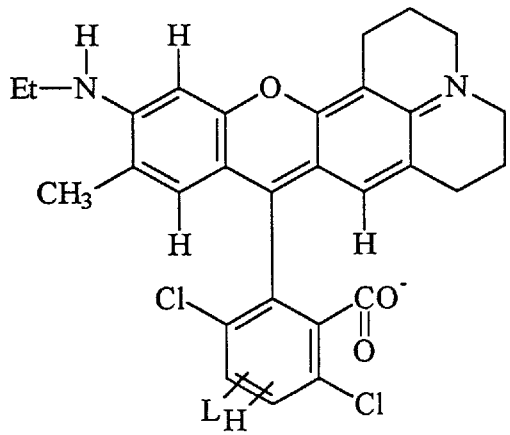
Figure 1F:
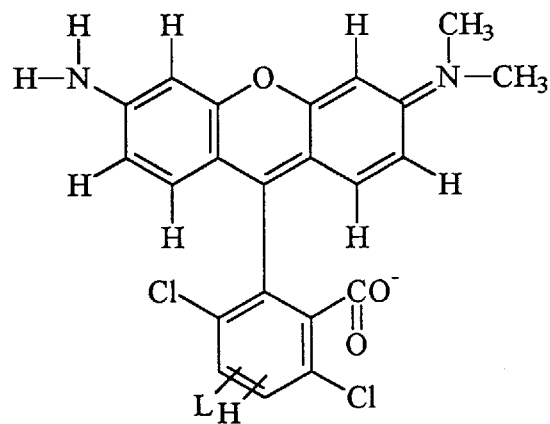

Several additional particularly preferred embodiments of the dye compounds of the invention are shown in FIGS. 1A and 1B. In compound 1a, $R_1$ is methyl, $R_2$–$R_6$ taken separately are hydrogen, one of $Y_1$ and $Y_2$ is ethyl, the other being hydrogen, $Y_3$ and $Y_4$ taken separately are hydrogen, $X_1$ is carboxylate, and one of $X_2$ and $X_3$ is linking group, the other being hydrogen. In compound 1b, $R_1$ is methyl, $R_2$–$R_6$ taken separately are hydrogen, one of $Y_1$ and $Y_2$ is ethyl, the other being hydrogen, $Y_3$ and $Y_4$ taken separately are methyl, $X_1$ is carboxylate, and, one of $X_2$ and $X_3$ is linking group, the other being hydrogen. In compound 1c, $R_1$, $R_2$, $R_5$, and $R_6$ taken separately are hydrogen, $Y_1$ and $Y_2$ taken separately are methyl, $R_3$ and $Y_3$ taken together are propano, $R_4$ and $Y_4$ taken together are propano, $X_1$ is carboxylate, and, one of $X_2$ and $X_3$ is linking group, the other being hydrogen. In compound 1d, $R_1$, $R_2$, $R_5$, and $R_6$ taken separately are hydrogen, $Y_1$ and $Y_2$ taken separately are hydrogen, $R_3$ and $Y_3$ taken together are propano, $R_4$ and $Y_4$, taken together are propano, $X_1$ is carboxylate, and one of $X_2$ and $X_3$ is linking group, the other being hydrogen. In compound 1e, $R_1$ is methyl, $R_2$, $R_5$ and $R_6$ taken separately are hydrogen, one of $Y_1$ and $Y_2$ is ethyl, the other being hydrogen, $R_3$ and $Y_3$ taken together are propano, $R_4$ and $Y_4$ taken together are propano, $X_1$ is carboxylate, and, one of $X_2$ and $X_3$ is linking group, the other being hydrogen. In compound 1f, $R_1$–$R_6$ taken separately are hydrogen, $Y_1$ and $Y_2$ taken separately are hydrogen, $Y_3$ and $Y_4$ taken separately are methyl, $X_1$ is carboxylate, and, one of $X_2$ and $X_3$ is linking group, the other being hydrogen.

FIGS. 8A–8H show preferred generalized synthesis schemes for the preparation of the 4,7-dichlororhodamine dyes of the invention. The variable substituents indicated in each figure are as previously defined.

FIGS. 8A–8D shows a generalized synthesis wherein the substituent $X_1$ can be other than carboxylate. In the figure, X' indicates moieties which are precursors to $X_1$. In the method of shown in FIGS. 8A–8D, two equivalents of a 3-aminophenol derivative FIGS. 8A/8B, such as 3-dimethylaminophenol, is reacted with one equivalent of a dichlorobenzene derivative FIG. 8C, e.g., 4-carboxy-3,6, dichloro-2-sulfobenzoic acid cyclic anhydride, i.e., where the $X_1$' moieties of 8c taken together are,

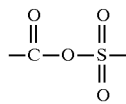

Figures 8A, 8B, 8C:
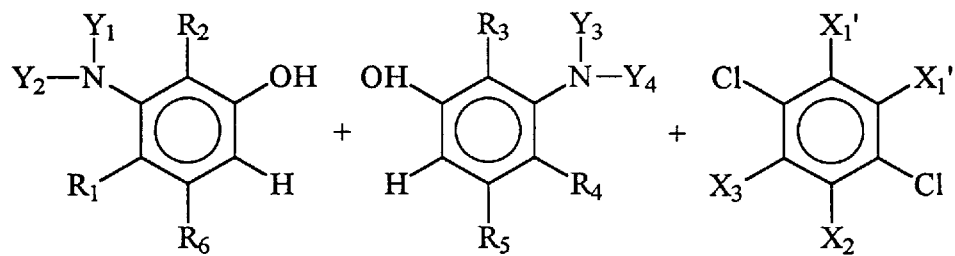
Figure 8D:
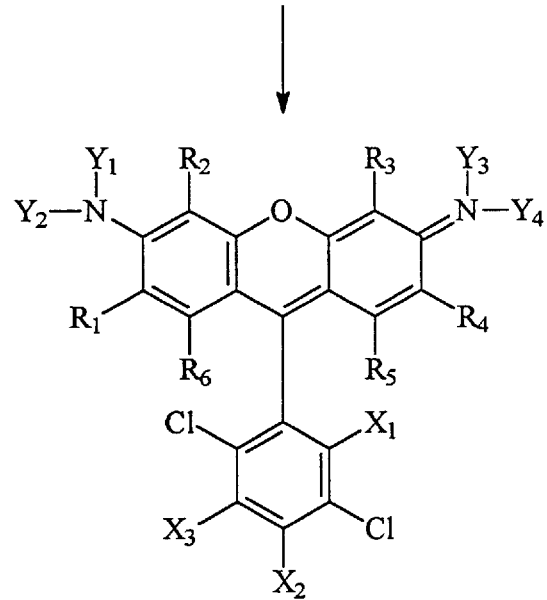

The reactants are then heated for 12 h in a strong acid, e.g., polyphosphoric acid or sulfuric acid, at 180° C. The crude dye FIG. 8D is precipitated by addition to water and isolated by centrifugation. To form a symetrical product, the substituents of reactants FIG. 8A and FIG. 8B are the same, while to form an asymetical product, the substituents are different.

Figure 8H:
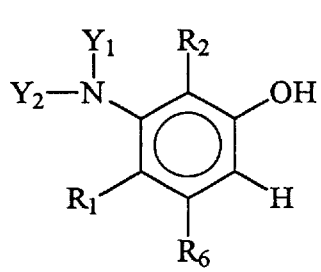
Figure 8H:
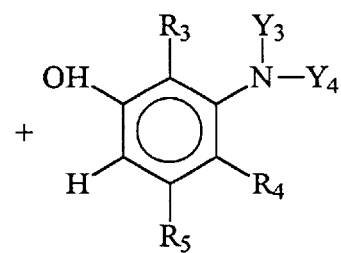
Figure 8H:
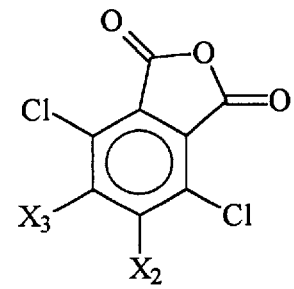
Figure 8H:
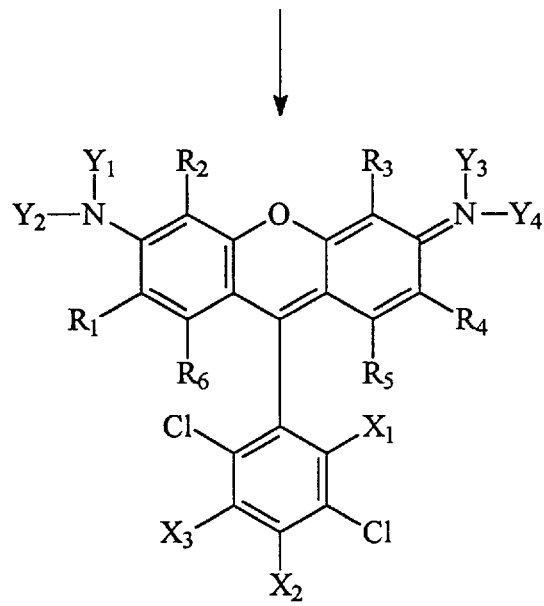

FIGS. 8E–8H shows a generalized synthesis wherein the substituent $X_1$ is carboxylate. In the method shown in FIGS. 8E–8H5, two equivalents of a 3-aminophenol derivative FIGS. 8E/8F, such as 3-dimethylaminophenol, is reacted with one equivalent of a phthalic anhydride derivative FIG. 8G, e.g. 3,6-dichlorotrimellitic acid anhydride. The reactants are then heated for 12 h in a strong acid, e.g., polyphosphoric acid or sulfuric acid, at 180° C. The crude dye FIG. 8H is precipitated by addition to water and isolated by centrifugation. To form a symetrical product, the substituents of reactants FIGS. 8E and 8F are the same, while to form an asymetical product, the substituents are different.

III. REAGENTS UTILIZING 4,7-DICHLORORHODAMINE DYE COMPOUNDS

In another aspect, the present invention comprises reagents labeled with the 4,7-dichlororhodamine dye compounds of Formula I. Reagents of the invention can be virtually anything to which the dyes of the invention can be attached. Preferably the dyes are covalently attached to the reagent directly or through a linkage. Exemplary reagents include proteins, polypeptides, polysaccharides, nucleotides, nucleosides, polynucleotides, lipids, solid supports, organic and inorganic polymers, and combinations and assemblages thereof such as chromosomes, nuclei living cells, such as bacteria, other microorganisms, mammalian cells, tissues, glycoproteins, and the like.

A. Nucleotide Reagents

A preferred class of reagents of the present invention comprise nucleotides and nucleosides which incorporate the asymmetric benzoxanthene dyes of the invention. Such nucleotide/side reagents are particularly useful in the context of labeling polynucleotides formed by enzymatic synthesis, e.g., nucleotide triphosphates used in the context of PCR amplification, Sanger-type polynucleotide sequencing, and nick-translation reactions.

Preferred nucleotidelside reagents of the present invention are shown below in Formula VI wherein

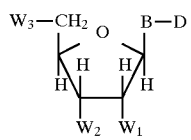

FORMULA VI

B is a nucleoside base, e.g., uracil, cytosine, deazaadenine, and deazaguanosine. $W_1$ and $W_2$ taken separately are H, OH, or —$OCH_3$, $W_3$ is OH, —$PO_4$, —$P_2O_7$, —$P_3O_{10}$, or analogs thereof, e.g., phosphorothioate, phosphoroanilidate, phosphoroanilothioate, phosphoramidiate, and other like phosphate analogs, including associated counterions if present, e.g., H, Na, $NH_4$, and the like. D is a dye compound of Formula I.

When B is purine or 7-deazapurine, the sugar moiety is attached at the $N^9$-position of the purine or deazapurine, and when B is pyrimidine, the sugar moiety is attached at the $N^1$-position of the pyrimidine.

The linkage linking B and D may be attached to D at any one of positions $R_1$–$R_6$ or $X_1$–$X_3$. Preferably, the linkage is attached at one of $X_2$ or $X_3$. Preferably, when B is a purine, the linkage linking B and D is attached to the 8-position of the purine, when B is 7-deazapurine, the linkage is attached to the 7-position of the 7-deazapurine, and when B is pyrimidine, the linkage is attached to the 5-position of the pyrimidine.

In one particularly preferred embodiment, the nucleotides of the present invention are dideoxynucleotide triphosphates having the structure shown below in Formula VII, including associated counterions if present.

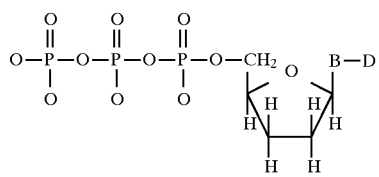

FORMULA VII

Labeled dideoxy nucleotides such as that shown in Formula VII find particular application as chain terminating agents, or "terminators", in Sanger-type DNA sequencing methods (Sanger).

In a second particularly preferred embodiment, the nucleotides of the present invention are deoxynucleotide triphosphates having the structure shown in Formula VIII below, including associated counterions if present.

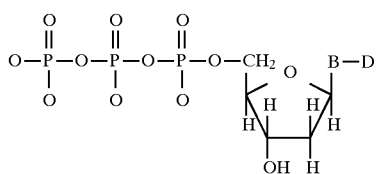
FORMULA VIII

Labeled deoxynucleotides such as that shown in Formula VIII find particular application as means for labeling polymerase extension products, e.g., in the polymerase chain reaction (Mullis).

Nucleotide/side labeling can be accomplished using any of a large number of known nucleoside/tide labeling techniques using known linking groups, and associated complementary functionalities to form linkages. See above for a discussion of preferred linking groups. The linkage lining the dye and nucleoside should (i) not interfere with oligonucleotide-target hybridization, (ii) be compatible with relevant enzymes, e.g., polymerases, ligases, and the like, and (ii) not quench the fluorescence of the dye.

In one preferred embodiment, the dyes of the invention are covalently linked to the 5-carbon of pyrimidine bases or to the 7-carbon of 7-deazapurine bases. Several suitable base labeling procedures have been reported that can be used with the invention. (Gibson; Gebeyehu; Haralambidis; Nelson 1992; Bergstrom; Fung 1988; Ward; Woo.)

Preferably, the linkages are acetylenic amido or alkenic amido linkages, the linkage between the dye and the nucleotide base being formed by reacting an activated NHS ester of the dye with an alkynylamino- or alkenylamino-derivatized base of a nucleotide. More preferably, the resulting linkage is 3-(carboxy)amino-1-propynyl or 3-amino-1-propyn-1-yl (Formula IX.1). Several preferred linkages for linking the dyes of the invention to a nucleoside base are shown below as Formulas IX.1, IX.2, and IX.3.

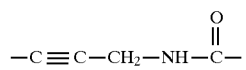
FORMULA IX.1

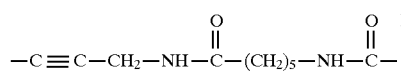
FORMULA IX.2

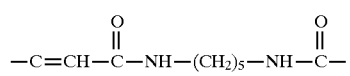
FORMULA IX.3

The synthesis of alkynylamino-derivatized nucleosides is described by (Hobbs 1989, 1992). Briefly, the alkynylamino-derivatized nucleotides are formed by placing the appropriate halodideoxynucleoside (usually 5-iodopyrimidine and 7-iodo-7-deazapurine dideoxynucleosides) and Cu(I) in a flask, flushing with argon to remove air, adding dry DMF, followed by addition of an alkynylamine, triethyl-amine and Pd(O). The reaction mixture is stirred for several hours, or until thin layer chromatography indicates consumption of the halodideoxynucleoside. When an unprotected alkynylamine is used, the alkynylaninonucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

B. Polynucleotide Reagents

Yet another preferred class of reagents of the present invention comprise polynucleotides labeled with the 4,7-dichlororhodamine dyes of the invention. Such labeled polynucleotides are useful in a number of important contexts including as DNA sequencing primers, PCR primers, oligonucleotide hybridization probes, and the like.

The polynucleotides of the invention include a nucleotide having the formula:

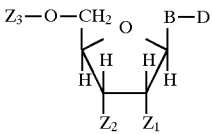
FORMULA X where B is a nucleotide base, e.g., 7-deazapurine, purine, or pyrimidine. $Z_1$ is H, OH or —$OCH_3$. $Z_2$ is OH, —$PO_4$, —$P_2O_7$, —$P_3O_{10}$, or analogs thereof, e.g., phosphorothioate, phosphoroanilidate, phosphoroanilothioate, phosphoramidiate, and other like phosphate analogs, including associated counterions if present, e.g., H, Na, $NH_4$, and the like, or Nuc, wherein Nuc refers to a nucleoside, nucleotide, or polynucleotide. The nucleotide of Formula X and Nuc are linked by a phosphodiester linkage or analog thereof, the linkage preferably being attached to the 5'-position of Nuc. $Z_3$ is H, —$PO_3$ or analogs thereof or Nuc, wherein Nuc and the nucleoside are linked by a phosphodiester linkage or analog thereof attached to the 3'-position of Nuc. D is a dye compound of Formula I. Base B is attached to the sugar moiety and to the dye compound as described above for the nucleotide reagent of the invention. As defined, the labeled nucleotide of Formula X can be the 5'-terminal nucleotide, the 3'-terminal nucleotide, or any internal nucleotide of the polynucleotide.

In one preferred embodiment, the polynucleotide of the present invention includes multiple dyes, at least one of which is a dye compound of the invention, located such that fluorescence energy transfer takes place between a donor dye and an acceptor dye. Such multi-dye polynucleotides find application as spectrally-tunable probes or DNA sequencing primers (Ju; Lee).

Labeled polynucleotides may be synthesized either enzymatically, e.g., using a DNA polymerase or ligase (Stryer), or by chemical synthesis, e.g., by the phosphoramidite method, the phosphite-triester method, and the like (Gait). Labels may be introduced during enzymatic synthesis utilizing labeled nucleotide triphosphate monomers as described above or may be introduced subsequent to synthesis.

Generally, if the labeled polynucleotide is made by enzymatic synthesis, the following procedure may be used. A template DNA is denatured and an oligonucleotide primer is annealed to the template DNA. A mixture of deoxynucleotide triphosphates and/or dideoxynucleotide triphosphates is added to the reaction including dGTP, DATP, dCTP, ddTTP, ddGTP, ddATP, ddCTP, and ddTTP, where at least a fraction of one of at least one the deoxynucleotides and/or dideoxynucleotides is labeled with a dye compound of the invention as described above. Next, a polymerase enzyme is added under conditions where its polymerase activity is operative. A labeled polynucleotide is formed by the incorporation of the labeled deoxynucleotides and/or dideoxynucleotides during polymerase strand synthesis. In an alternative enzymatic synthesis method, two primers are used instead of one, one primer complementary to the +strand and the other complementary to the—strand of the target, the polymerase is a thermostable polymerase, and the reaction temperature is cycled between a denaturation temperature and an extension temperature, thereby exponentially synthesizing a labeled complement to the target sequence by PCR (Mullis; Innis).

Subsequent to synthesis, the polynucleotide may be labeled at a number of positions including the 5'-terminus (Eckstein; Orgel; Smith); the phosphodiester backbone (Eckstein); or at the 3'-terminus (Nelson 1992a; Nelson 1992b; Nelson 1995). For a through review of oligonucleotide labeling procedures see (Steiner).

In one preferred post-synthesis chemical labeling method an oligonucleotide is labeled as follows. A dye including a carboxylate linking group is converted to the NHS ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10–20x) to an aminohexyl derivatized oligonucleotide in 0.25M bicarbonate/carbonate buffer at pH 9.4 and allowed to react for 6 hours (Fung 1988). The dye labeled oligonucleotide is separated from unreacted dye by passage through a size-exclusion chromatography column eluting with buffer, e.g., 0.1 molar triethylamine acetate (TEAA). The fraction containing the crude labeled oligonucleotide is further purified by reverse phase HPLC employing gradient elution.

IV. METHODS UTILIZING COMPOUNDS AND REAGENTS OF THE INVENTION

The dyes and reagents of the present invention are well suited to methods utilizing fluorescent detection, particularly methods requiring the simultaneous detection of multiple spatially-overlapping analytes. Dyes and reagents of the invention are particularly well suited for identifying classes of polynucleotides that have been subjected to a biochemical separation procedure, such as electrophoresis, where a series of bands or spots of target substances having similar physiochemical properties, e.g. size, conformation, charge, hydrophobicity, or the like, are present in a linear or planar arrangement. As used herein, the term "bands" includes any spatial grouping or aggregation of analytes on the basis of similar or identical physiochemical properties. Usually bands arise in the separation of dye-polynucleotide conjugates by electrophoresis.

Classes of polynucleotides can arise in a variety of contexts. In a preferred category of methods referred to herein as "fragment analysis" or "genetic analysis" methods, labeled polynucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography, and, the separated fragments are detected subsequent to the separation, e.g., by laser-induced fluorescence. In a particularly preferred embodiment, multiple classes of polynucleotides are separated simultaneously and the different classes are distinguished by spectrally resolvable labels.

One such fragment analysis method known as amplified fragment length polymorphism detection (AmpFLP) is based on amplified fragment length polymorphisms, i.e., restriction fragment length polymorphisms that are amplified by PCR (Vos). These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphates in the PCR Another exemplary fragment analysis method is based on variable number of tandem repeats, or VNTRs (Webber; Caskey). VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2–4 bases) repeated sequence. One of the most abundant interspersed repetitive DNA families in humans is the (dC-dA)n—(dG-dT)n dinucleotide repeat family (also called the (CA)n dinucleotide repeat family). There are thought to be as many as 50,000 to 100,000 (CA)n repeat regions in the human genome, typically with 15–30 repeats per block. Many of these repeat regions are polymorphic in length and can therefore serve as useful genetic markers. Preferably, in VNTR or STR methods, a dye label is introduced into the polynucleotide fragments by using a dye-labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes (Fung 1989). Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination method, i.e., dideoxy DNA sequencing, or Sanger sequencing. This method involves the synthesis of a DNA strand by a DNA polymerase in vitro using a single-stranded or double-stranded DNA template whose sequence is to be determined. Synthesis is initiated at only the one site where an oligonucleotide primer anneals to the template. The synthesis reaction is terminated by incorporation of a nucleotide analog that will not support continued DNA elongation. The chain-terminating nucleotide analogs are typically 2',3'-dideoxynucleoside 5'-triphosphates (ddNTPs) which lack the 3'-OH group necessary for 3' to 5' DNA chain elongation. When proper proportions of dNTPs (2'-deoxynucleoside 5'-triphosphates) an d one of the four ddNTPs are used, enzyme-catalyzed polymerization will be terminated in a fraction of the population of chains at each site where the ddNTP can be incorporated. If labeled primers or labeled ddNTPs are used for each reaction, the sequence information can be detected by fluorescence after separation by high-resolution electrophoresis. In the chain termination method, dyes of the invention can be attached to either sequencing primers or dideoxynucleotides.

In each of the above fragment analysis methods labeled polynucleotides are preferably separated by electrophoretic procedures (Rickwood and Hames; Osterman) Preferably the type of electrophoretic matrix is crosslinked or uncrosslinked polyacrylamide having a concentration (weight to volume) of between about 2–20 weight percent.

More preferably, the polyacrylide concentration is between about 4–8 percent. Preferably in the context of DNA sequencing in particular, the electrophoresis matrix includes a strand separating, or denaturing, agent, e.g., urea, formamide, and the like. Detailed procedures for constructing such matrices are given by (Maniatis 1980; Maniatis 1975; *ABI PRISM™ 377 DNA Sequencer User's Manual*). The optimal polymer concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations.

Subsequent to electrophoretic separation, the dye-polynucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or the 532 emission line of a neodymium solid-state YAG laser. Several argon ion lasers are available commercially which lase simultaneously at these lines, e.g., the Model 2001 from Cyonics, Ltd. (Sunnyvale, Calif.). The fluorescence is then detected by a light-sensitive detector, e.g., a photomultiplier tube, a charged coupled device, or the like.

V. EXAMPLES

The invention will be further clarified by a consideration of the following examples, which are intended to be purely exemplary of the invention and not to in any way limit its scope. All reagents were purchased from Aldrich Chemical Co. (Milwaukee, Wis.) except as otherwise indicated. The 3,6-dichlorotrimellitic anhydride was prepared as described by (Khanna).

Example 1

Preparation of DR110 (Formula II)

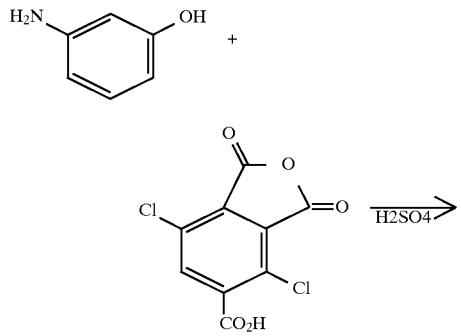

-continued

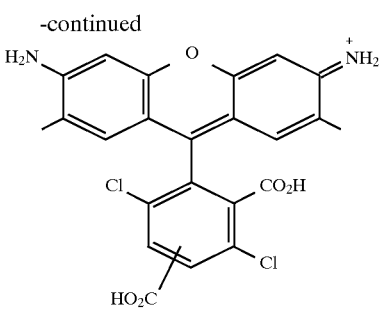

A mixture of 3-aminophenol (0.25 g, 2.3 mmol), 3,6-dichlorotrimellitic anhydride (0.33 g, 1.3 mmol) and sulfuric acid (1 mL) were combined and heated to 190° C. for 12 h. Water (10 mL) was added to the reaction and the resulting black solid separated by filtration. The solid was then extracted with acetonitrile (10 mL). The resulting orange solution was concentrated to dryness and the residue dissolved in carbonate/bicarbonate buffer (250 mM pH 9, 10 mL). The solution was acidified with concentrated HCl, the red precipitate collected by centrifugation and dried in a vacuum centrifuge. A red solid was obtained (32 mg, 5% yield). The absorbance maximum of a solution of the DR110 product in 40% acetonitrile/triethylammonium acetate buffer was 516 nm.

Example 2

Preparation of DTMR (Formula IV)

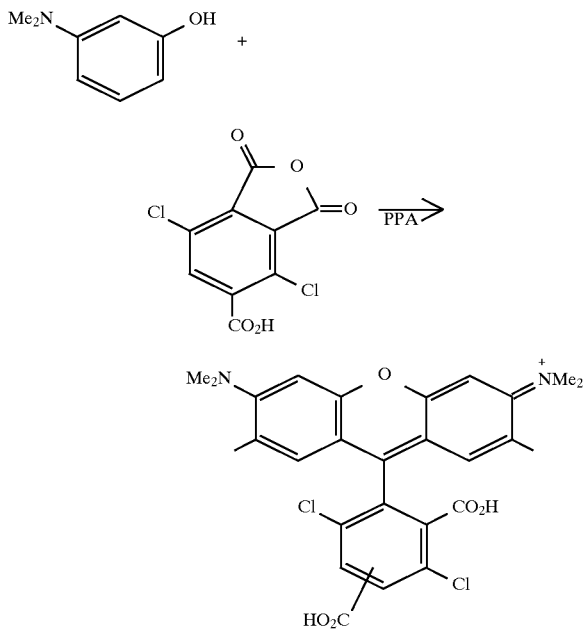

A mixture of 3-dimethylaminophenol (0.5 g, 3.6 mmol), 3,6-dichlorotrimellitic anhydride (500 mg, 1.9 mmol) and polyphosphoric acid (PPA) (5 g) were combined and heated to 180° C. for 12 h. Water (20 mL) was added to the red-brown reaction and the mixture filtered and washed with 5% HCl. A dark solid was obtained (79 mg, 0.15 mmol, 8% yield). The absorbance maximum of a solution of the DTMR product in 40% acetonitrile/triethylammonium acetate buffer was 570 nm.

Example 3

Preparation of DROX (Formula V)

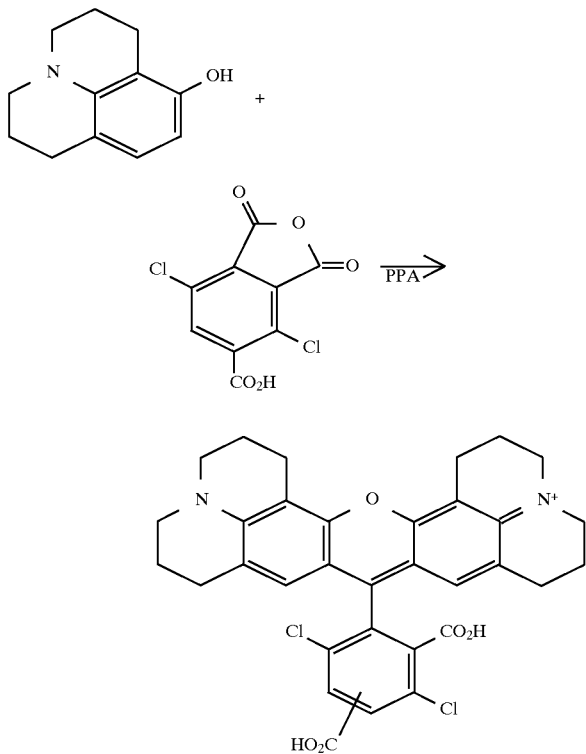

A mixture of 8-hydroxyjulolidine (140 mg, 0.73 mmol), 3,6-dichlorotrimellitic anhydride (100 mg, 0.38 mmol) and polyphosphoric acid (1 g) were combined and heated to 180° C. for 16 h. Water (10 mL) was added and the solution was filtered. The solid was washed with aqueous HCl and dried to yielding 87 mg of purple solid (0.14 mmol, 37%).

Example 4

Preparation of DR6G (Formula III)

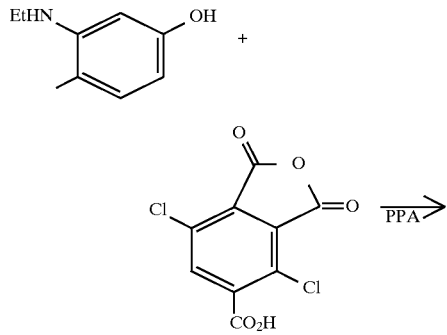

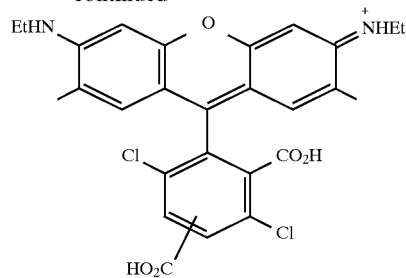

A mixture of 3-aminomethyl-p-cresol (100 mg, 0.66 mmol), 3,6-dichlorotrimellitic anhydride (100 mg, 0.38 mmol) and polyphosphoric acid (0.5 g) were combined and heated to 180° C. for 12 h. Water (10 mL) was added to the red-brown reaction and the mixture filtered. The solid was taken up in 1M carbonate/bicarbonate buffer (pH 9, 25 mL) and filtered. The filtrate was acidified with concentrated HCl and the solid collected by centrifugation and dried. The solid was extracted with acetonitrile (10 mL) and the extracts were concentrated to a sticky solid. The solid was dissolved in dimethylformamide (0.6 mL). The yield was estimated by diluting an aliquot into 40% acetonitrile/triethylammonium acetate buffer and measuring the absorbance in a UV/Visible spectrophotometer. Using an extinction coefficient of 50,000 $cm^{-1}$ $M^{-1}$, the absorbance maximum was found to be 540 nm and the yield to be 9%.

Example 5

Preparation of the NHS Ester of DR6G

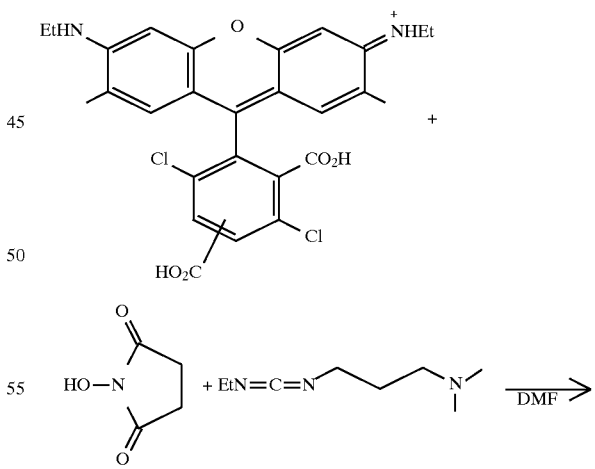

21

-continued

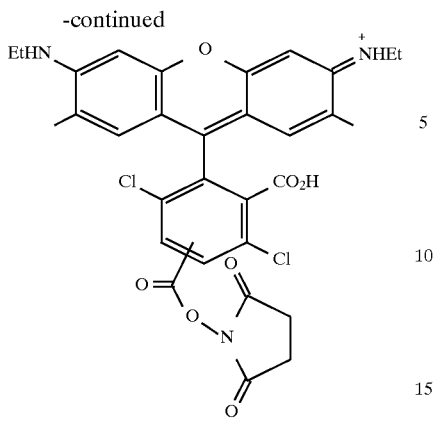

A solution of DR6G in dimethylformamide (6 μmol in 0.1 mL) was combined with N-hydroxysuccinimide (22 mg, 0.2 mmol) and 1-(3-dimethylaminopropyl)-3-ethylcarbodiimide hydrochloride (12 mg, 0.06 mmol). Reaction progress was monitored by thin-layer chromatography on silica gel using a mixture of dichloromethane, methanol and acetic acid (600:60:16) as eluant. After the starting material was consumed, the reaction was diluted with dichloromethane (10 mL) and washed with 5% HCl (10 mL). The material which was insoluble in both phases was discarded. The organic phase was washed successively with 250 mM carbonate/bicarbonate (10 mL) and with 5% HCl (10 mL). The solution was dried ($MgSO_4$) and concentrated to a dark oil. The residue was taken up in dimethylformamide (0.2 mL) and stored at $-20°$ C.

After three days at $-20°$ C., gold-reflecting crystals had formed in the dimethylformamide solution. The supernatant was decanted and discarded. The residue was dissolved in methylsulfoxide (0.1 mL). An aliquot was diluted into 40% acetonitrile/triethylammonium acetate buffer. Using an extinction coefficient of 50,000 $cm^{-1}$ $M^{-1}$, the absorbance maximum was found to be 548 nm and the yield to be 7%.

Example 6

Preparation of DR6G-Labeled Dideoxyadenosinetriphosphate

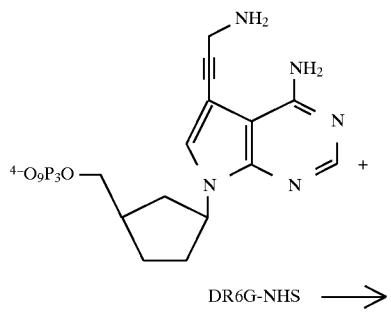

DR6G-NHS $\longrightarrow$

22

-continued

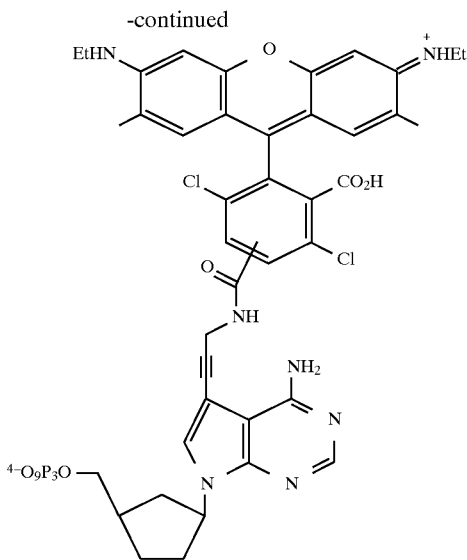

A solution of $ddATP-NH_2$ (5 μL, 20 mM 0.1 μmol) (Hobbs 1989, 1992), DR6G-NHS (0.15 μmol) and 250 mM carbonate/bicarbonate buffer, pH 9 (5 μL) were mixed. After 10 min at room temperature the solution was subjected to HPLC with an anion-exchange column and eluted with a gradient of 40% acetonitrile/60% 0.1M triethylammonium bicarbonate to 40% acetonitrile/60% 1.5M triethylammonium bicarbonate to remove free dye. The fraction containing dye-labeled nucleotide and unlabeled nucleotide was concentrated in a vacuum centrifuge and subjected to a second HPLC using a reverse-phase column. The unlabeled nucleotide and each dye isomer of dye-labeled nucleotide were separated using an elution gradient of 15% acetonitrile/85% 0.1M triethylammonium acetate to 35% acetonitrile/65% 0.1M triethylammonium acetate. The solutions containing dye-labeled nucleotide were concentrated in a vacuum centrifuge, redissolved in 10 mM carbonate/bicarbonate buffer, pH 9, and quantified by measuring the absorbance of the solution in a UV/Visible spectrophotometer. Yields were approximately 1%.

Example 7

Preparation of Dye-Labeled Oligonucleotide

A solution of 5'-aminohexyl-functionalized oligonucleotide, (10 μL, 1 mM) and DR6G-NHS (10 μL, 12 mM in methylsulfoxide) and carbonate/bicarbonate buffer (2 μL, 1M) were combined. The aminohexyl derivatized primer was prepared by automated solid-phase DNA synthesis using Aminolink-2 in the last cycle of the synthesis (PE Applied Biosystems p/n 400808). After 10 min at room temperature the solution was subjected to gel filtration on Sephadex G-25 to separate free dye. The fraction containing dye-labeled oligonucleotide and unlabeled oligonucleotide was collected and subjected to HPLC purification on a reverse-phase column. The unlabeled oligonucleotide and each dye isomer of dye-labeled oligonucleotide were separated using an elution gradient of 10% acetonitrile/85% 0.1M triethylammonium acetate to 30% acetonitrile/65% 0.1M triethylammonium acetate. The solutions containing dye-labeled oligonucleotide were concentrated in a vacuum centrifuge, and redissolved in a buffer containing 10 mM Tris, 1 mM EDTA, pH 7.0 (TE).

23

Example 8

Single-Color Sequencing Reactions Utilizing the 4, 7-Dichlororhodamine Dideoxynucleotide Terminators of the Invention Dye terminator reactions were done with AmpliTaq® DNA Polymerase, FS following the basic protocols in the ABI PRISM™ Dye Terminator Cycle Sequencing Core Kit Manual (PE Applied Biosystems p/n 402116). (The FS enzyme is a recombinant thermus aquaticus DNA polymerase having two point mutations—G46D and F667Y). All reagents except the dNTP mix and dye terminators were from an ABI PRISM™ Dye Terminator Cycle Sequencing Core Kit (PE Applied Biosystems p/n 402117). A premix of reaction components was prepared as follows, where volumes are on a per reaction basis:

| | |
|---|---|
| 5X Buffer | 4 µL |
| dNTP mix | 1 µL |
| Template:pGEM ®-3Zf(+), 0.2µg/µL | 5 µL |
| Primer: −21 M13 (forward), 0.8 pmol/µL | 2 µL |
| AmpliTaq DNA Polymerase,FS | 0.5 µL |
| $H_2O$ | 2.5 µL |

Reactions were set up in 0.5 ml tubes for the Perkin-Elmer 480 DNA Thermal Cycler (PE Applied Biosystems p/n N801-100). Total reaction volumes were 20 µL, including 15 µL of the above reaction premix, an appropriate amount of dye labeled terminator, and water. Single color dye terminator reactions were set up with either 1 pmole of dye terminator for A and G terminators or with 15 pmole of dye terminator for C and T terminators. In a few cases, the dye terminators for C or T were at too low a concentration, such that 5 µL resulted in less than 15 pmole of dye terminator. In these cases, 5 µL of dye terminator was used and no water was added to the reaction. 30 µL of mineral oil was added to the top of each reaction volume to reduce evaporation during thermocycling.

Reactions were thermocycled as follows:

| |
|---|
| 96° C. 30 sec |
| 50° C. 15 sec |
| 60° C. 4 min for 25 cycles | followed by a 4° C. hold cycle.

All reactions were purified by spin-column purification on Centri-Sep spin columns (Princeton Separations, Adelphia, N.J., p/n CS-901). Gel material in the column was hydrated with 0.8 mL of deionized water for at least 30 minutes at room temperature. After the columns were hydrated, and it was apparent that no bubbles were trapped in the gel material, the upper-end cap and then the lower-end cap were removed. The column was allowed to drain by gravity. Columns were then inserted into the wash tubes provided in the Centi-Sep kit and centrifuged in a variable speed microcentrifuge (Eppendorf Model 5415) at 1300×g for 2 minutes. Columns were removed from the wash tubes and inserted into sample collection tubes. The reaction mixture was carefully removed from under the oil using a glass pipette and loaded on top of the Centri-Sep column. Columns were centrifuged in a variable speed microcentrifuge (Eppendorf Model 5415) at 1300×g for 2 minutes. Samples were dried in a vacuum centrifuge.

The dried samples were resuspended in 25 µL of Template Suppression Reagent (PE Applied Biosystems p/n 401674), vortexed, heated to 95° C. for 2 minutes, cooled on ice, vortexed again, and centrifuged (13,000×g). 10 µL of the purified sample was aliquoted into sample vials (PE Applied Biosystems p/n 401957) adapted for use with the PE ABI PRISM™ 310 Genetic Analyzer (PE Applied Biosystems p/n 310-00-100/120). Electrophoresis on the Model 310 used a 61 cm long, 50 µm ID uncoated fused silica capillary having a length to the detector of 50 cm (PE Applied Biosystems p/n 402840). The capillary was filled with a solution of a linear dimethylpolyacrylamide (DMA) sieving polymer (Madabhushi), buffer, and containing nucleic acid denaturants (PE Applied Biosystems p/n 402837). Samples were electrokinetically injected for 30 sec at 2.5 kV. Electrophoresis was performed for 2 hr at 12.2 kV with the capillary temperature maintained at 42° C.

FIGS. 3A–3H show electropherograms of single color C-termination reactions using several different dideoxy terminators of the invention. Labels were attached to the C-terminal dideoxynucleotide terminator. Bases 12–82 of PGEM-3Zf(+) are shown in each electropherogram. The particular dye labels used in each electropherogram are indicated in the following table:

| FIG. | Dye Attached to ddC Terminator |
|---|---|
| 3A | 6ROX |
| 3B | DR110 |
| 3C | DR6G-1 |
| 3D | DR6G-2 |
| 3E | DTMR-1 |
| 3F | DTMR-2 |
| 3G | DROX-1 |
| 3H | DROX-2 |

(The "1" and "2" designations indicate the particular dye isomer being used. The 1 and 2 isomers are defined by the elution order of free dye in a reverse-phase separation system utilizing a C-8 column and an elution gradient of 15% acetonitrile/85% 0.1M triethylammonium acetate to 35% acetonitrile/65% 0.1M triethylammonium acetate.)

FIGS. 4A–4G show electropherograms of single color T-termination reactions using several different dideoxy terminators of the invention. Labels were attached to the T-terminal dideoxynucleotide terminator. Bases 7–84 of PGEM-3Zf(+) are shown in each electrophoerogram. The particular labels used for each electropherogram are indicated in the following table:

| FIG. | Dye Attached to ddT Terminator |
|---|---|
| 4A | 6TMR |
| 4B | DR110 |
| 4C | DR6G-1 |
| 4D | DR6G-2 |
| 4E | DTMR-1 |
| 4F | DTMR-2 |
| 4G | DROX-1 |

FIGS. 5A–5I show electropherograms of single color A-termination reactions using several different dideoxy terminators of the invention. Labels were attached to the A-terminal dideoxynucleotide terminator. Bases 94–167 of PGEM-3Zf(+) are shown in each electropherogram. The particular labels used for each electropherogram are indicated in the following table:

| FIG. | Dye Attached to ddA Terminator |
|---|---|
| 5A | 5R6G |
| 5B | DR110-1 |
| 5C | DR110-2 |
| 5D | DR6G-1 |
| 5E | DR6G-2 |
| 5F | DTMR-1 |
| 5G | DTMR-2 |
| 5H | DROX-1 |
| 5I | DROX-2 |

FIGS. 6A–6H show electropherograms of single color G-termination reactions using several different dideoxy terminators of the invention. Labels were attached to the G-terminal dideoxynucleotide terminator. Bases 185–252 of PGEM-3Zf(+) are shown in each electropherogram. The particular labels used for each electropherogram are indicated in the following table:

| FIG. | Dye Attached to ddG Terminator |
|---|---|
| 6A | 5R110 |
| 6B | DR110 |
| 6C | DR6G-1 |
| 6D | DR6G-2 |
| 6E | DTMR-1 |
| 6F | DTMR-2 |
| 6G | DROX-1 |
| 6H | DROX-2 |

The preceding data indicate that the dye-labeled dideoxy terminators of the invention are suitable for use in fluorescence-based Sanger-type DNA sequencing.

Example 9

Four-Color Sequencing Reactions Utilizing the 4,7-Dichlororhodamine Dideoxynucleotide Terminators of the Invention The Four color DNA sequencing reactions were prepared and analyzed essentially as described above in Example 8.

Figure 2A:
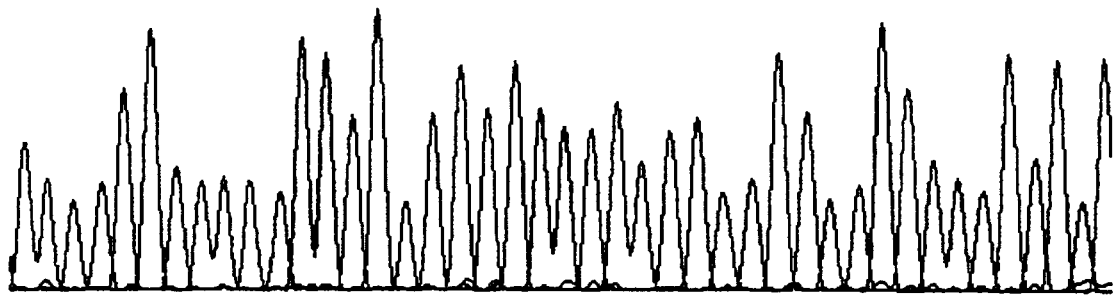
FIGS. 2A and 2B show electropherograms of 4-color sequencing reactions using dye-labeled dideoxy terminators (2A) and dye-labeled primers (2B) of the invention.

FIG. 2A shows an electropherogram of a four-color sequencing reaction in which the four dideoxynucleotide terminators were labeled as follows: ddG with DR110 dye, ddA with DR6G-2 dye, ddC with DTMR-1 dye, and ddT with DROX-1 dye. The Figure shows bases 196–238 of the PGEM® template.

Example 10

Four-Color Sequencing Reactions Utilizing the 4,7-Dichlororhodamine Oligonucleotide Primers of the Invention Dye primer reactions were performed using AmpliTaq® DNA Polymerase, FS as generally described in ABI PRISM™ Dye Primer Cycle Sequencing Core Kit Manual (PE Applied Biosystems, p/n 402114). All reagents except the primer and template were from an ABI PRISM™ Dye Primer Cycle Sequencing Core Kit (PE Applied Biosystems p/n 402125). Dye-labeled −21 M13 primers were dissolved at a concentration of 0.4 pmoles/μL. The primers were labeled as follows: C reaction with DR110; A reaction with DR6G; G reaction with DTMR; and T reaction with DROX. A premix of reaction components was prepared for each of the four base reactions as follows (Quantities given are per reaction):

|  | A(μL) | C(μL) | G(μL) | T(μL) |
|---|---|---|---|---|
| 5X Buffer | 1 | 1 | 2 | 2 |
| ddNTP/dNTP | 1 | 1 | 2 | 2 |
| Dye Primer | 1 | 1 | 2 | 2 |
| AmpliTaq DNA Polymerase,FS | 0.17 | 0.17 | 0.34 | 0.34 |
| H$_2$O | 0.83 | 0.83 | 1.66 | 1.66 |

The M13mp18 sequencing template was dissolved at a concentration of at 0.05 μg/μL.

Sequencing reactions were set up as follows in 0.2 mL thin-walled Gene Amp 9600 DNA Thermalcycler tubes (PE Applied Biosystems p/n N801-0540).

|  | A(μL) | C(μL) | G(μL) | T(μL) |
|---|---|---|---|---|
| Premix | 4 | 4 | 8 | 8 |
| Template | 1 | 1 | 2 | 2 |

Reactions were cycled using the following temperature profile:

| | |
|---|---|
| 96° C. 10 sec; | |
| 55° C. 5 sec | |
| 70° C. 1 min | for 15 cycles | followed by

| | |
|---|---|
| 96° C. 10sec | |
| 70° C. 1 min | for 15 cycles | followed by a 4° C. hold cycle.

The four reactions were combined in 80 μL 95% ethanol, allowed to sit on ice for 10 min, and centrifuged for 15 min at maximum speed in a microcentrifuge. The ethanol supernatant was removed and the pellet dried in a vacuum centrifuge.

Figure 2B:
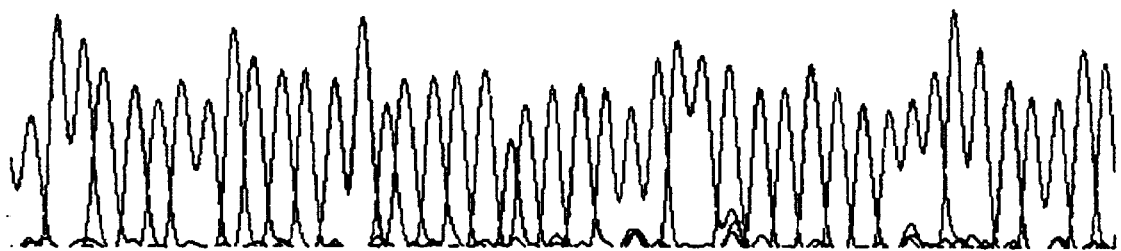
Figure 3A:
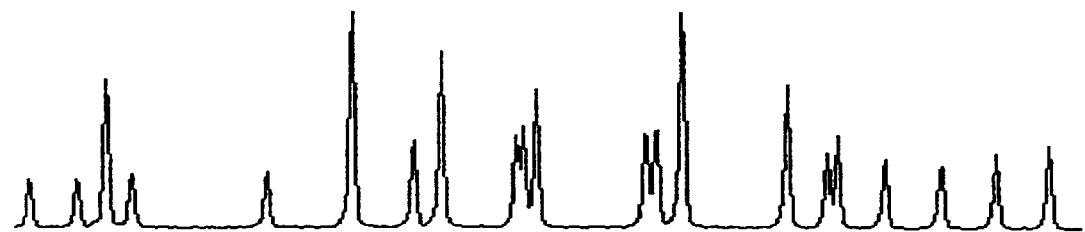
FIGS. 3A–3H show electropherograms of single color C-termination reactions using several different dideoxy terminators of the invention.
Figure 3B:
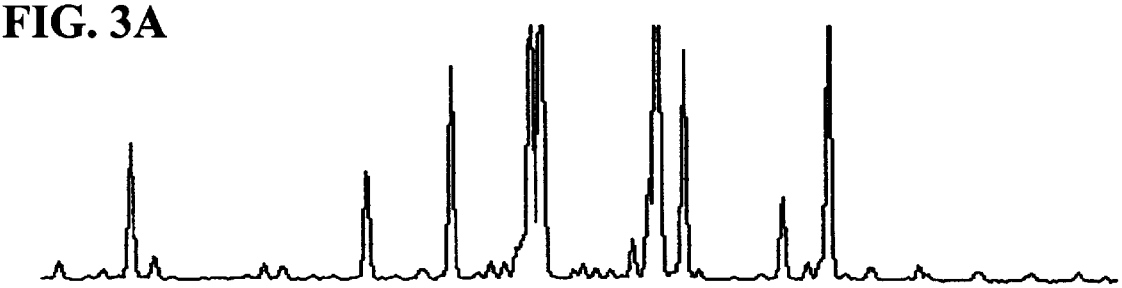
Figure 3C:
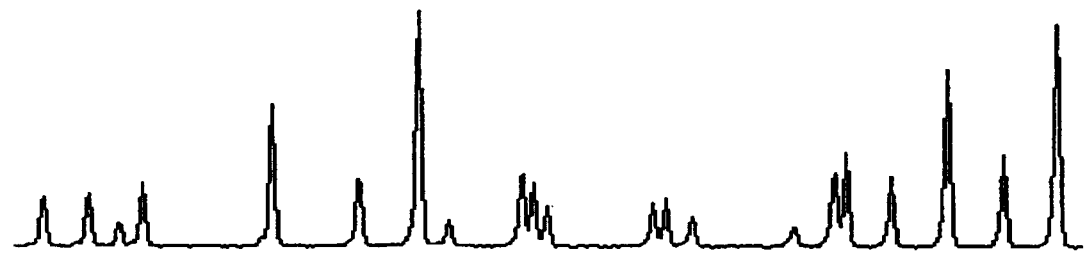
Figure 3D:
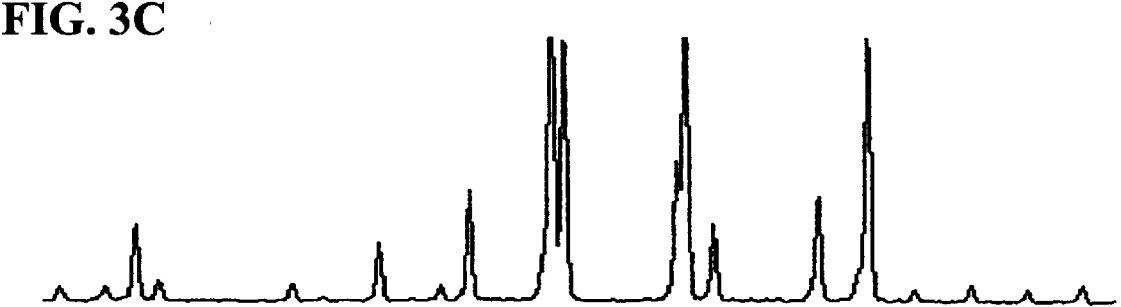
Figure 3E:
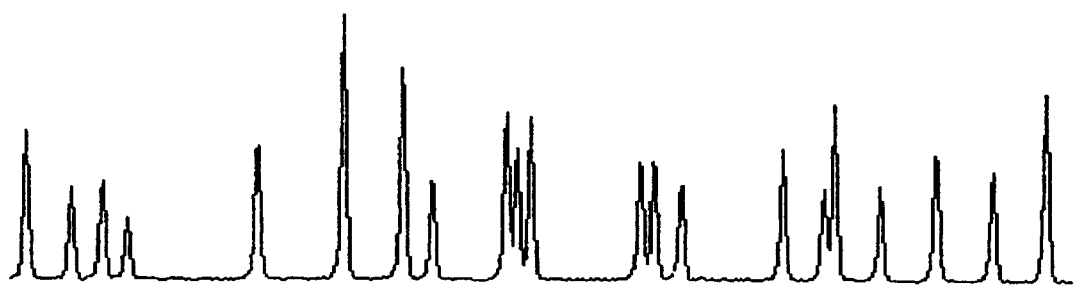
Figure 3F:
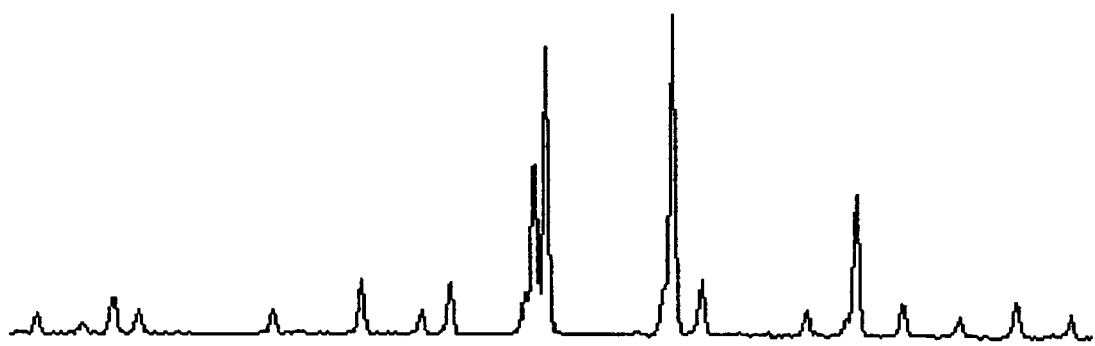
Figure 3G:
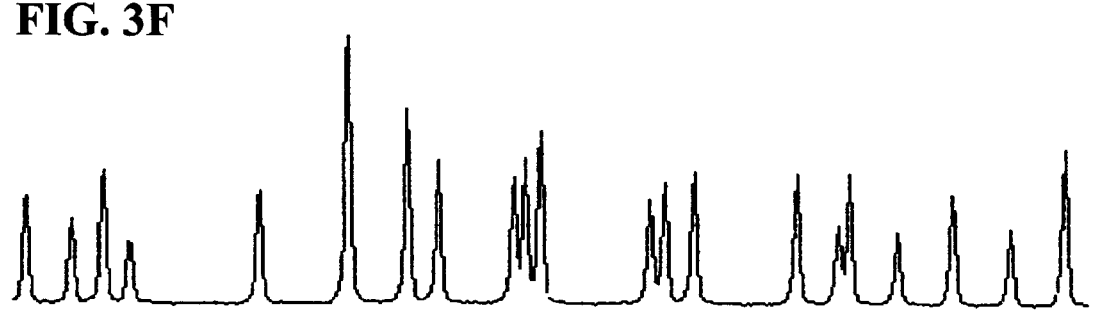
Figure 3H:
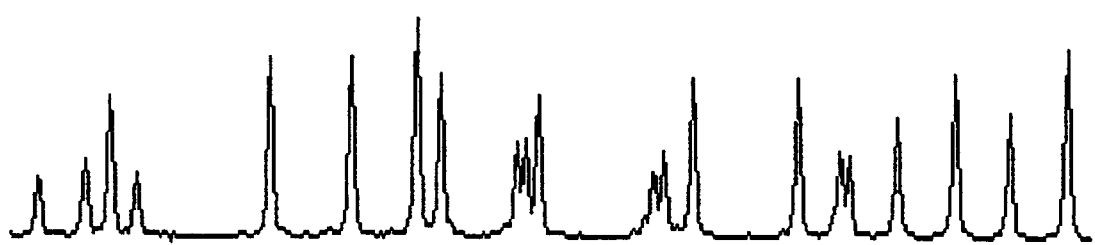
Figure 4A:
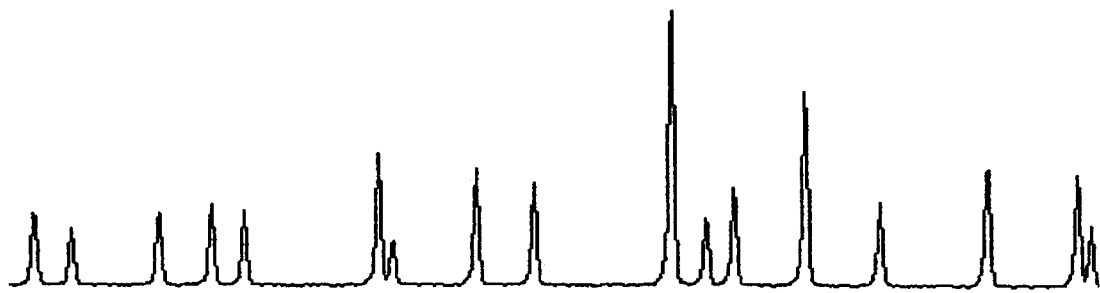
FIGS. 4A–4G show electropherograms of single color T-termination reactions using several different dideoxy terminators of the invention.
Figure 4B:
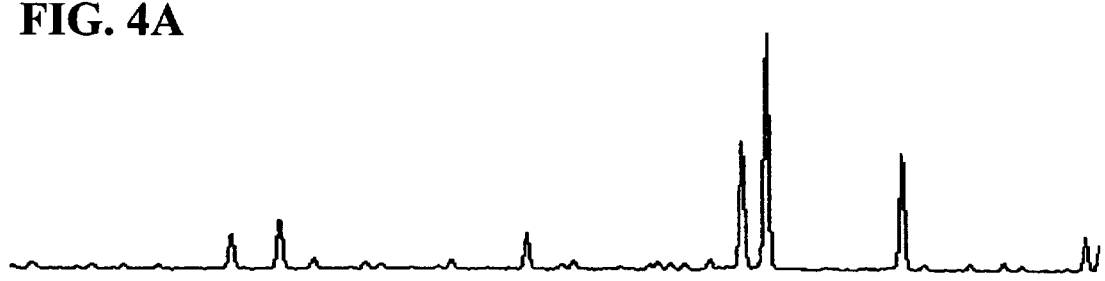
Figure 4C:
Figure 4D:
Figure 4E:
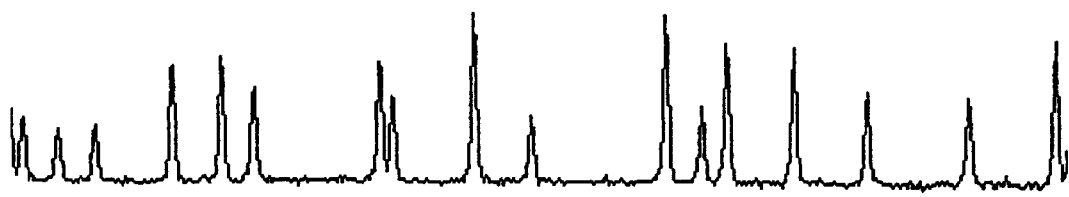
Figure 4F:
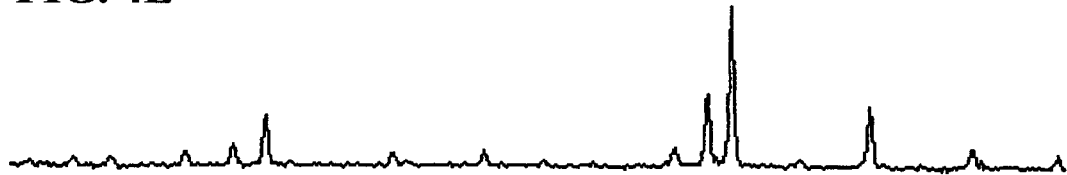
Figure 4G:
Figure 5A:
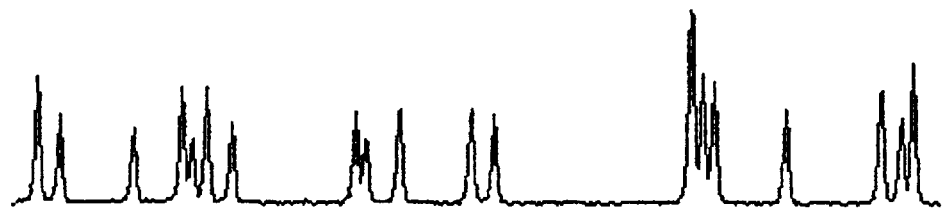
FIGS. 5A–5I show electropherograms of single color A-termination reactions using several different dideoxy terminators of the invention.
Figure 5B:
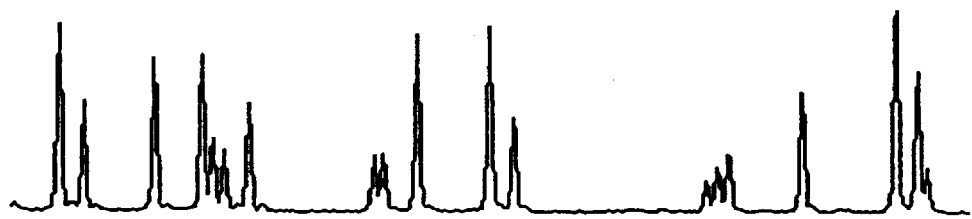
Figure 5C:
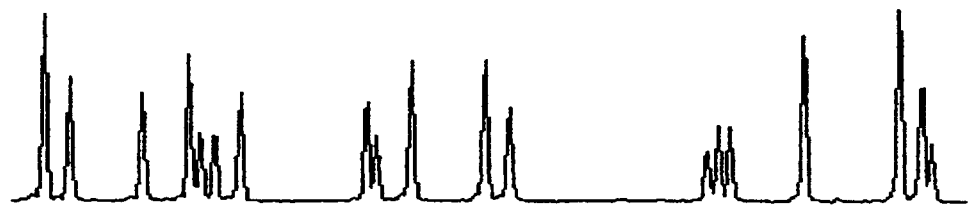
Figure 5D:
Figure 5E:
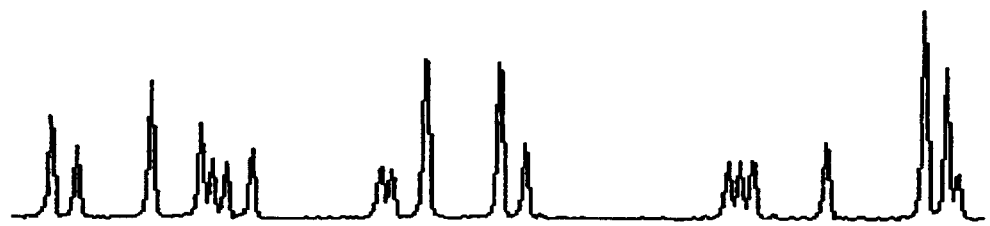
Figure 5F:
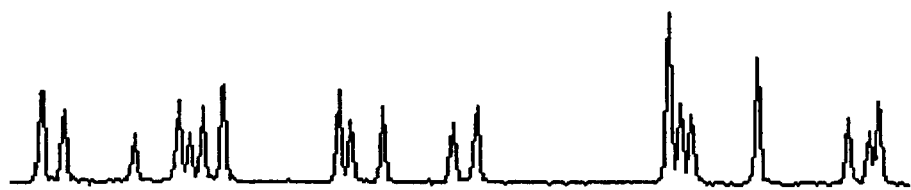
Figure 5G:
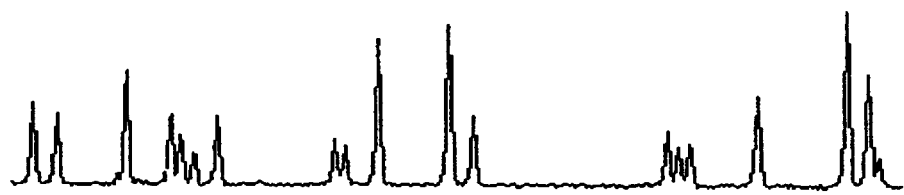
Figure 5H:
Figure 5I:
Figure 6A:
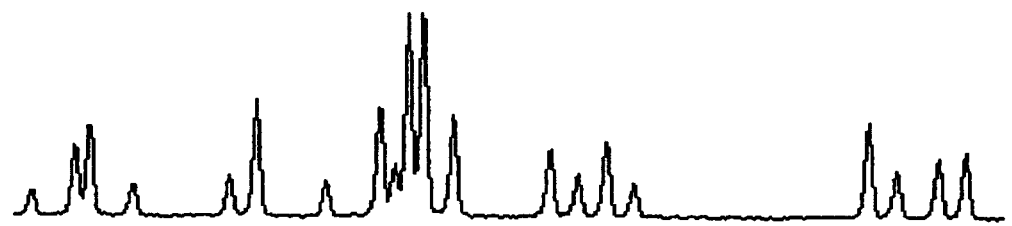
FIGS. 6A–6H show electropherograms of single color G-termination reactions using several different dideoxy terminators of the invention.
Figure 6B:
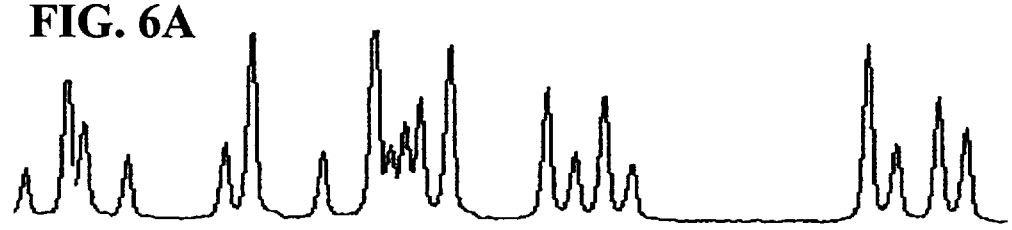
Figure 6C:
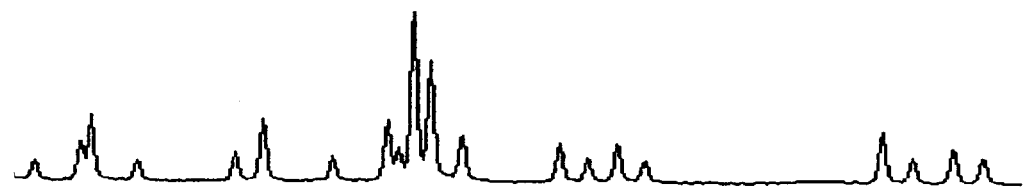
Figure 6D:
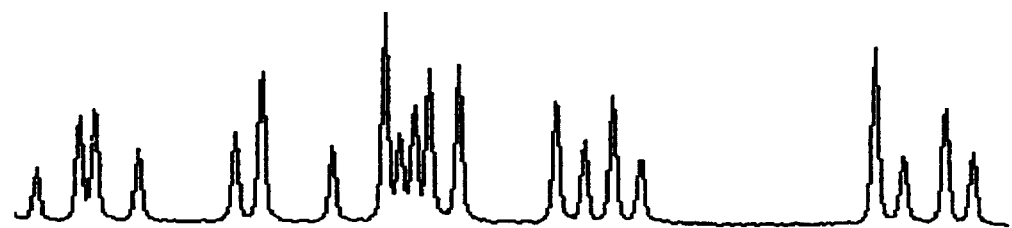
Figure 6E:
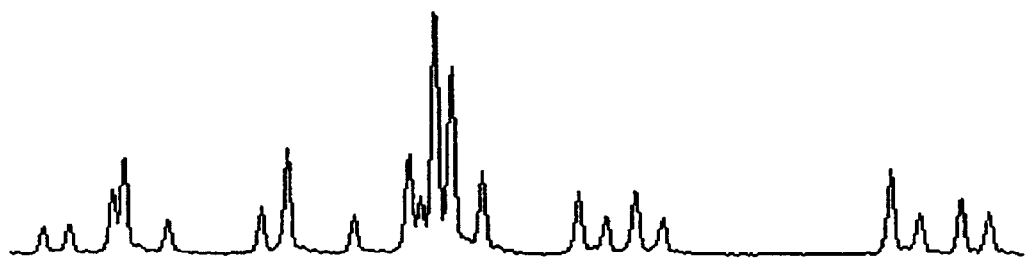
Figure 6F:
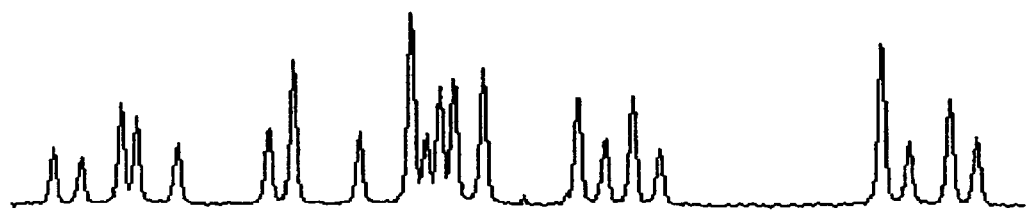
Figure 6G:
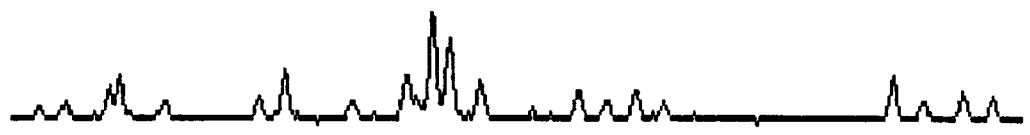
Figure 6H:
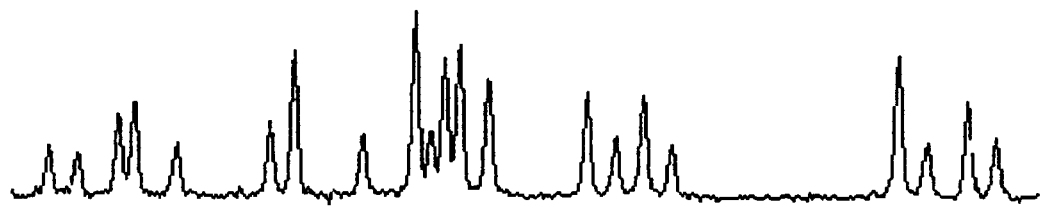

The pellets were resuspended in 6 μL loading buffer and analyzed on an ABI PRISM™ Model 377 DNA Sequencer (PE Applied Biosystems p/n 377-01-200/208) using either the standard filter set A or a modified filter set with longer wave-length settings. FIG. 2B shows a sampling of the resulting data from base 50 to base 93.

Example 11

Comparison of Fluorescence Emission Spectra of Traditional Rhodamines and the 4,7,-Dichlororhodamines of the Present Invention Emission spectra for oligonucleotides labeled with traditional rhodamines were compared with emission spectra for oligonucleotides labeled with the 4,7-dichlororhodamines of the present invention. The concentration of each labeled oligonucleotide was 0.4 μM in TE buffer. Excitation of the rhodamine dyes was at 488 nm and excitation of the 4,7-dichlororhodamine dyes was at 500 nm. Spectra were each normalized to the emission maximum. Measurements were made using a Perkin-Elmer LS-50 instrument.

Figure 7A:
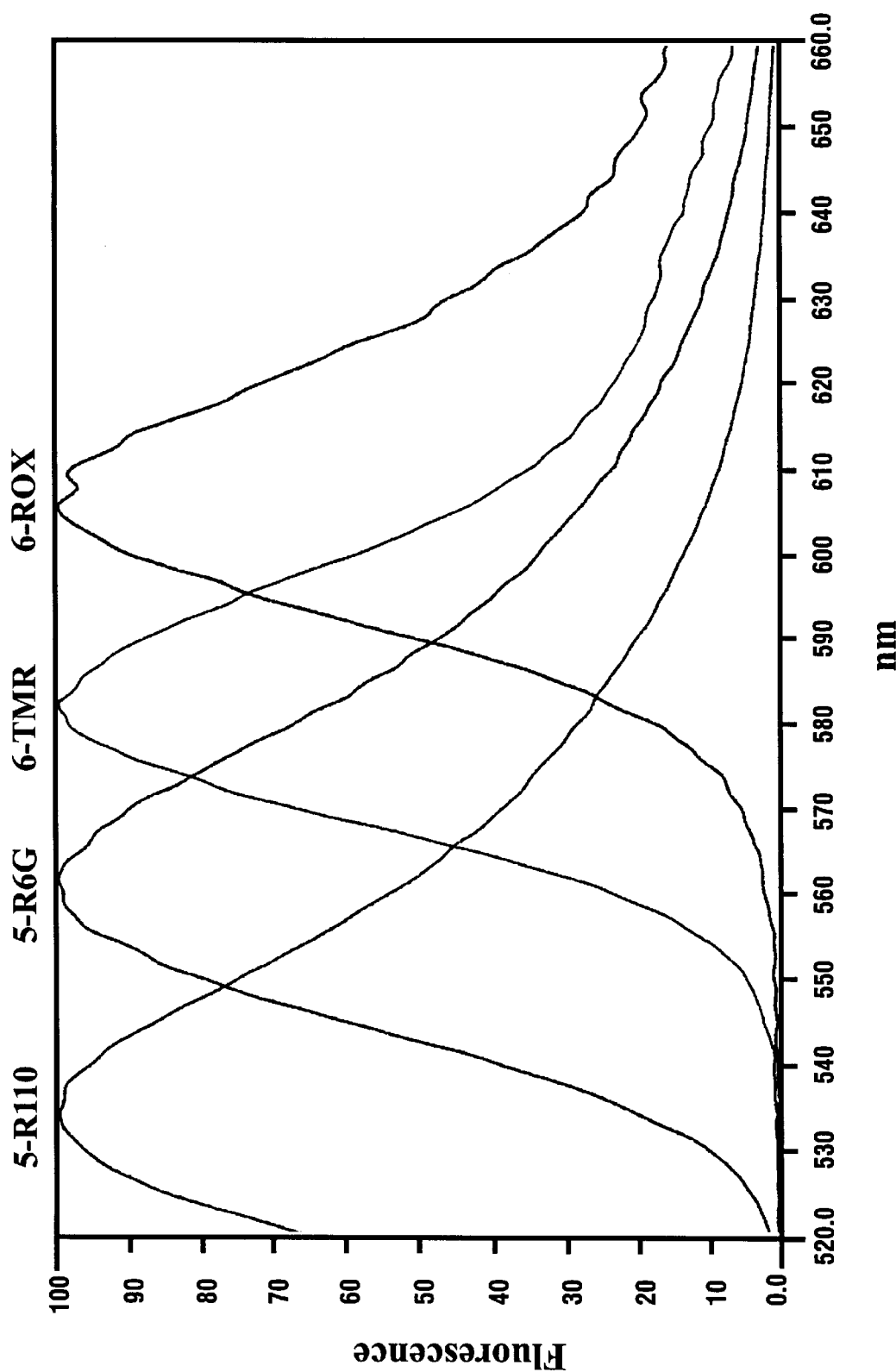
FIGS. 7A and 7B compare fluorescence emission spectra of oligonucleotides labeled with existing rhodamine compounds (7A) and several preferred 4,7-dichlororhodamine-oligonucleotide compounds of the present invention (7B).
Figure 7B:
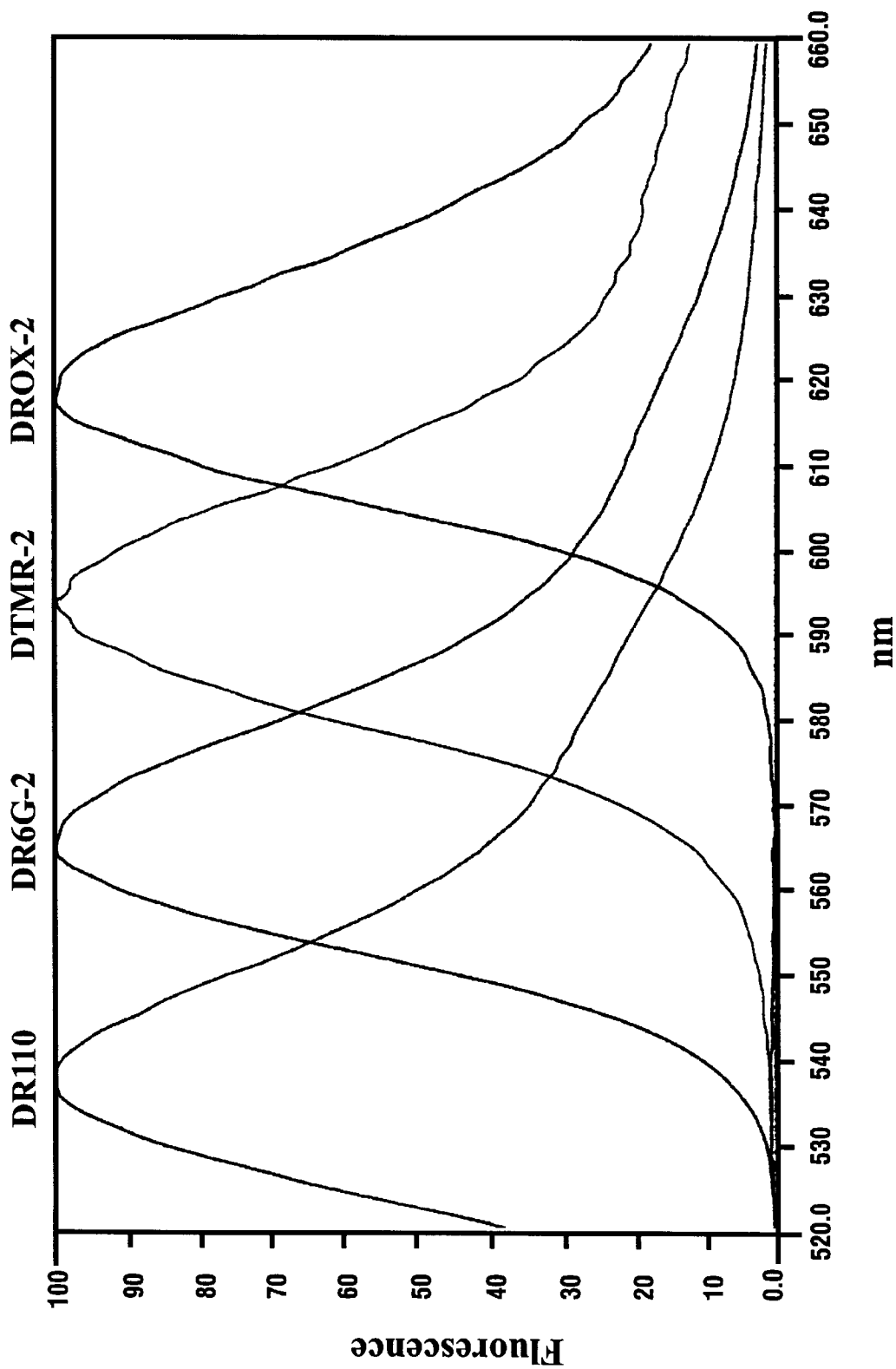

FIG. 7A shows the emission spectra of the four known rhodamine dyes 5-R110, 5-R6G, 6-TMR, and 6-ROX (Bergot). FIG. 7B shows the emission spectra of four preferred 4,7-dichlororhodamine dyes of the invention DR110, DR6G-2, DTMR-2, and DROX-2. This reduced width of the emission spectra for the 4,7-dichlororhodamine dyes results in an increased ability to perform multicomponent analysis techniques required when multiple spatially-overlapping species are to be detected.

All publications and patent applications are herein incorporated by reference to the same extent as if each individual publication or patent application was specifically and individually indicated to be incorporated by reference.

Although only a few embodiments have been described in detail above, those having ordinary skill in the organic chemical art will clearly understand that many modifications are possible in the preferred embodiment without departing from the teachings thereof All such modifications are intended to be encompassed within the following claims.

We claim:

1. A compound having the formula:

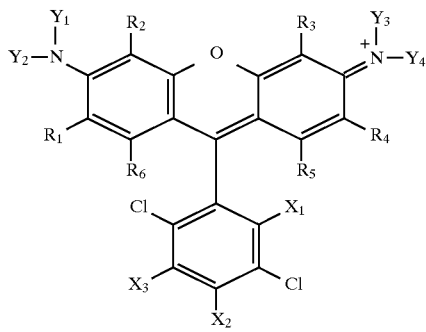

wherein:
$R_1$–$R_6$ taken separately are selected from the group consisting of hydrogen, fluorine, chlorine, lower alkyl, lower alkene, lower alkyne, sulfonate, sulfone, amino, amido, nitrile, lower alkoxy, linking group, and combinations thereof, or, when taken together, $R_1$ and $R_6$ is benzo, or, when taken together, $R_4$ and $R_5$ is benzo;
$Y_1$–$Y_4$ taken separately are selected from the group consisting of hydrogen and lower alkyl or, when taken together, $Y_1$ and $R_2$ is propano and $Y_2$ and $R_1$ is propano, or, when taken together, $Y_3$ and $R_3$ is propano and $Y_4$ and $R_4$ is propano; and
$X_1$–$X_3$ taken separately are selected from the group consisting of hydrogen, chlorine, fluorine, lower alkyl, carboxylate, sulfonic acid, —CH$_2$OH, and linking group.

2. The compound of claim 1 wherein $X_1$ is carboxylate.

3. The compound of claim 1 wherein one of $X_2$ and $X_3$ is linking group.

4. The compound of claim 1 wherein $R_2$ and $R_3$ taken separately are hydrogen.

5. The compound of claim 1 wherein:
$R_1$–$R_6$ taken separately are selected from the group consisting of hydrogen, methyl, and ethyl, or, when taken together, $R_1$ and $R_6$ is benzo, or when taken together, $R_4$ and $R_5$ is benzo;
$Y_1$–$Y_4$ taken separately are selected from the group consisting of hydrogen, methyl, and ethyl, or, when taken together, $Y_1$ and $R_2$ is propano and $Y_2$ and $R_1$ is propano, or, when taken together, $Y_3$ and $R_3$ is propano and $Y_4$ and $R_4$ is propano;
$X_1$ is carboxylate; and
$X_2$ and $X_3$ taken separately are selected from the group consisting of hydrogen and linking group.

6. The compound of claim 1 wherein:
$R_1$–$R_6$ taken separately are hydrogen;
$Y_1$–$Y_4$ taken separately are hydrogen;
$X_1$ is carboxylate; and
one of $X_2$ and $X_3$ is linking group, the other being hydrogen.

7. The compound of claim 1 wherein:
$R_1$ and $R_4$ taken separately are methyl;
$R_2$, $R_3$, $R_5$, and $R_6$ are hydrogen;
one of $Y_1$ and $Y_2$ is ethyl, the other being hydrogen;
one of $Y_3$ and $Y_4$ is ethyl, the other being hydrogen;
$X_1$ is carboxylate; and
one of $X_2$ and $X_3$ is linking group, the other being hydrogen.

8. The compound of claim 1 wherein:
$R_1$–$R_6$ taken separately are hydrogen;
$Y_1$–$Y_4$ taken separately are methyl;
$X_1$ is carboxylate; and
one of $X_2$ and $X_3$ is linking group, the other being hydrogen.

9. The compound of claim 1 wherein:
$R_1$ and $Y_2$ taken together are propano;
$R_2$ and $Y_1$ taken together are propano;
$R_3$ and $Y_3$ taken together are propano;
$R_4$ and $Y_4$ taken together are propano;
$R_5$ and $R_6$ are hydrogen;
$X_1$ is carboxylate; and
one of $X_2$ and $X_3$ is linking group, the other being hydrogen.

10. The compound of claim 1 wherein:
$R_1$ is methyl;
$R_2$–$R_6$ taken separately are hydrogen;
one of $Y_1$ and $Y_2$ is ethyl, the other being hydrogen;
$Y_3$ and $Y_4$ taken separately are hydrogen;
$X_1$ is carboxylate; and
one of $X_2$ and $X_3$ is linking group, the other being hydrogen.

11. The compound of claim 1 wherein:
$R_1$ is methyl;
$R_2$–$R_6$ taken separately are hydrogen;
one of $Y_1$ and $Y_2$ is ethyl, the other being hydrogen;
$Y_3$ and $Y_4$ taken separately are methyl;
$X_1$ is carboxylate; and
one of $X_2$ and $X_3$ is linking group, the other being hydrogen.

12. The compound of claim 1 wherein:
$R_1$, $R_2$, $R_5$, and $R_6$ taken separately are hydrogen;
$Y_1$ and $Y_2$ taken separately are methyl;
$R_3$ and $Y_3$ taken together are propano;
$R_4$ and $Y_4$ taken together are propano;
$X_1$ is carboxylate; and
one of $X_2$ and $X_3$ is linking group, the other being hydrogen.

13. The compound of claim 1 wherein:
$R_1$, $R_2$, $R_5$, and $R_6$ taken separately are hydrogen;
$Y_1$ and $Y_2$ taken separately are hydrogen;
$R_3$ and $Y_3$ taken together are propano;

$R_4$ and $Y_4$, taken together are propano;

$X_1$ is carboxylate; and one of $X_2$ and $X_3$ is linking group, the other being hydrogen.

14. The compound of claim 1 wherein:

$R_1$ is methyl;

$R_2$, $R_5$ and $R_6$ taken separately are hydrogen;

one of $Y_1$ and $Y_2$ is ethyl, the other being hydrogen;

$R_3$ and $Y_3$ taken together are propano;

$R_4$ and $Y_4$ taken together are propano propano;

$X_1$ is carboxylate; and one of $X_2$ and $X_3$ is linking group, the other being hydrogen.

15. The compound of claim 1 wherein:

$R_{1-R6}$ taken separately are hydrogen;

$Y_1$ and $Y_2$ taken separately are hydrogen;

$Y_3$ and $Y_4$ taken separately are methyl;

$X_1$ is carboxylate; and one of $X_2$ and $X_3$ is linking group, the other being hydrogen.

* * * * *